United States Patent
Weindorf et al.

(10) Patent No.: US 11,187,692 B2
(45) Date of Patent: Nov. 30, 2021

(54) ENHANCED CHEMICAL CHARACTERIZATION OF SOLID MATRICES USING X-RAY FLUORESCENCE AND OPTICAL COLOR REFLECTANCE

(71) Applicant: Texas Tech University System, Lubbock, TX (US)

(72) Inventors: David Weindorf, Lubbock, TX (US); Delaina Pearson, Greenville, SC (US); Somsubhra Chakraborty, West Bengal (IN)

(73) Assignee: Texas Tech University System, Lubbock, TX (US)

(*) Notice: Subject to any disclaimer, the term of this patent is extended or adjusted under 35 U.S.C. 154(b) by 0 days.

(21) Appl. No.: 17/038,058

(22) Filed: Sep. 30, 2020

(65) Prior Publication Data

US 2021/0080443 A1     Mar. 18, 2021

Related U.S. Application Data

(60) Continuation-in-part of application No. 16/715,374, filed on Dec. 16, 2019, now Pat. No. 10,900,946, (Continued)

(51) Int. Cl.
*G01J 3/00*     (2006.01)
*G01N 33/24*    (2006.01)
(Continued)

(52) U.S. Cl.
CPC .......... *G01N 33/246* (2013.01); *G01J 3/4406* (2013.01); *G01N 21/274* (2013.01);
(Continued)

(58) Field of Classification Search
CPC ...... G01J 3/02; G01J 3/28; G01J 3/42; G01N 21/31; G01N 21/552
(Continued)

(56) References Cited

U.S. PATENT DOCUMENTS

| | | |
|---|---|---|
| 5,446,681 A | 8/1995 | Gethner et al. |
| 6,697,665 B1 | 2/2004 | Rava et al. |

(Continued)

FOREIGN PATENT DOCUMENTS

KR     10-0899011     11/2008

OTHER PUBLICATIONS

Akaike, H. "Information theory and the extension of the maximum likelihood principle." In: Petrov, V.N., Csaki, F. (Eds.), 2nd International Symposium on Information Theory. Academiai Kiadó, Budapest, 1973, pp. 267-281.

(Continued)

*Primary Examiner* — Md M Rahman
(74) *Attorney, Agent, or Firm* — Daniel J. Chalker; Edwin S. Flores; Chalker Flores, LLP

(57) ABSTRACT

An apparatus or method determines a content of the one or more elements of a solid matrix by scanning the solid matrix using a PXRF spectrometer and a color sensor, receiving a PXRF spectra from the PXRF spectrometer and a numerical color data from the color sensor, extracting a value for each of the one or more elements the PXRF spectra, determining the content of the one or more elements of the solid matrix using one or more processors and a predictive model that relates the value of each of the one or more elements and the numerical color data to the content of the one or more elements of the solid matrix, and providing the content of the one or more elements of the solid matrix to one or more input/output interfaces.

34 Claims, 11 Drawing Sheets

Related U.S. Application Data which is a division of application No. 16/165,472, filed on Oct. 19, 2018, now Pat. No. 10,697,953, which is a continuation-in-part of application No. 15/319,816, filed as application No. PCT/US2015/036537 on Jun. 18, 2015, now Pat. No. 10,107,770.

(60) Provisional application No. 62/912,387, filed on Oct. 8, 2019, provisional application No. 62/575,498, filed on Oct. 22, 2017, provisional application No. 62/013,692, filed on Jun. 18, 2014.

(51) Int. Cl.
*G01N 23/223* (2006.01)
*G01N 21/359* (2014.01)
*G01N 21/27* (2006.01)
*G01J 3/44* (2006.01)

(52) U.S. Cl.
CPC ......... *G01N 21/359* (2013.01); *G01N 23/223* (2013.01); *G01N 2223/076* (2013.01); *G01N 2223/304* (2013.01); *G01N 2223/33* (2013.01)

(58) Field of Classification Search
USPC ....................................................... 356/300
See application file for complete search history.

(56) References Cited

U.S. PATENT DOCUMENTS

| | | |
|---|---|---|
| 2004/0186383 A1 | 9/2004 | Rava et al. |
| 2006/0291619 A1 | 12/2006 | Statham |
| 2012/0033220 A1 | 2/2012 | Kotidis et al. |
| 2012/0158315 A1 | 6/2012 | Trygstad et al. |
| 2017/0122888 A1 | 5/2017 | Heckner et al. |
| 2017/0122889 A1 | 5/2017 | Weindorf et al. |
| 2018/0188225 A1 | 7/2018 | Rossel et al. |
| 2019/0257774 A1 | 8/2019 | Seidler et al. |

OTHER PUBLICATIONS

Aldabaa, A.A.A. et al. "Combination of proximal and remote sensing methods for rapid soil salinity quantification." Geoderma 2015, 239-240, 34-46.
Auchmoody, L.R., et al. "Revegetation of a brine-killed forest site." Soil Sci. Soc. Am. J. 1988, 52, 277-280.
Barreiros, M.A., et al. "Application of total-reflection XRF to elemental studies of drinking water", X-Ray Spectrom. 1997, 26, 165-168.
Berg, M. et al. "Arsenic contamination of groundwater and drinking water in Vietnam: A human health threat." Environmental Science & Technology 2001, 35(13), 2621-2626.
Bettinelli, M., et al. "Determination of heavy metals in soils and sediments by microwave-assisted digestion and inductively coupled plasma optical emission spectrometry analysis." Analytica Chimica Acta 2000, 424, 289-296.
Brevik, E.C. et al. "The past, present, and future of soils and human health studies." Soil 2015, 1, 35-46. http://dx.doi.org/10.5194/soil-1-35-2015.
Chakraborty, S., et al. "Semi-quantitative evaluation of secondary carbonates via portable X-ray fluorescence spectrometry." Soil Sci. Soc. Am. J. 2017a, 81, 844-852.
Chakraborty, S. et al. "Predicting soil arsenic pools by visible near infrared diffuse reflectance spectroscopy." Geoderma 2017a, 296, 30-37.
Chakraborty, S., et al. "Rapid assessment of regional soil arsenic pollution risk via diffuse reflectance spectroscopy." Geoderma 2017b, 289, 72-81.
Chang, C., Laird, et al. "Near infrared reflectance spectroscopy: principal components regression analysis of soil properties." Soil Sci. Soc. Am. J. 2001, 65, 480-490.
Clark, J.J. et al. "Extent, characterization, and sources of soil lead contamination in small-urban residential neighborhoods." Environ. Qual. 2014, 42, 1498-1506.
Eksperiandova, L.P., et al. "Analysis of waste water by x-ray fluorescence spectrometry." X-Ray Spectrometry 2002, 31 (3), 259-263.
Gazley, M.F., et al. "A review of the reliability and validity of portable X-ray fluorescence spectrometry (pXRF) data." In: Monograph 23, Mineral Resource and Ore Reserve Estimation, second edition AusIMM, 2014, pp. 69-82.
Hanna-Attisha, M., et al. "Elevated blood lead levels in children associated with the Flint drinking water crisis: A spatial analysis of risk and public health response " American Journal of Public Health 2016, 106(2), 283-290.
Kar, D., et al. "Assessment of heavy metal pollution in surface water." International Journal of Environmental Science & Technology 2008, 5(1), 119-124.
Koch, J., et al. "Proximal sensor analysis of mine tailings in South Africa: An exploratory study." Journal of Geochemical Exploration 2017 (Accepted; In Press) https://doi.org/10.1016/j.gexplo.2017.06.020.
Kuo, S. "Phosphorus. In: Sparks et al. (Eds.), Methods of Soil Analysis—Part 3, Chemical Methods." Soil Science Society of America, Madison, WI, 1996, pp. 869-919.
McGladdery, C. et al. "Elemental assessment of vegetation via portable Xray fluorescence (PXRF) spectrometry." J. Environ. Manage. 2018 (Accepted; In Press).
McLaren, T.I. et al. "Rapid, nondestructive total elemental analysis of Vertisol soils using portable X-ray fluorescence." Soil Sci. Soc. Am J. 2012a, 76, 1436-1445.
McLaren, T.I. et al. "A rapid and nondestructive plant nutrient analysis using portable X-ray fluorescence." Soil Sci. Soc. Am. J. 2012, 76, 1446-1453.
Moncur, M.C. et al. "Long-term mineralogical and geochemical evolution of sulfide-rich mine tailings under a shallow watercover." Appl. Geochem. 2015, 57, 178-193.
Muggeo, V.M.R. "Segmented: an R package to tit regression models with broken-line relationships." R News 2008, 8(1), 20-25.
Muhammad, S. et al. "Health risk assessment of heavy metals and their apportionment in drinking water of Kohistan region, northern Pakistan." Michochemical Journal 2011, 98, 334-343.
Nordstrom, D.K. "Worldwide occurrences of arsenic in ground water." Science 2002, 296 (5576), 2143-2145.
O'Rourke, S.M. et al. "An assessment of model averaging to improve predictive power of portable vis-NIR and XRF for the determination of agronomic soil properties." Geoderma 2016, 279, 31-44.
Paulette, L. et al. "Rapid assessment of soil and contaminant variability via portable x-ray fluorescence spectroscopy: Copşa Mică, Romania." Geoderma 2015, 243-244, 130-140.
Pearson, D. et al. "Water analysis via portable X-ray fluorescence spectrometry." Journal of Hydrology 2017, 544, 172-179.
Peinado, F.M. et al. "A rapid field procedure for screening trace elements in polluted soil using portable X-ray fluorescence (PXRF)." Geoderma 2010, 159, 76-82.
Pen-Mouratov, S. et al. "Influence of Industrial heavy metal pollution on soil free-living nematode population." Environ. Pollut. 2008, 152, 172-183.
Razo, I. et al. "Arsenic and heavy metal pollution of soil, water, and sediments in a semi-arid climate mining area in Mexico." Water, Air, and Soil Pollution 2004, 152, 129-152.
Reidinger, S. et al. "Rapid and accurate analyses of silicon and phosphorus in plants using a portable X-ray fluorescence spectrometer." New Phytologist 195, 699-706. Rengasamy, P., 2006. World salinization with emphasis on Australia. J. Exp. Bot. 2012, 57, 1017-1023.
Rhoades, J.D. "Salinity: electrical conductivity and total dissolved solids. In: Sparks et al. (Eds.), Methods of Soil Analysis—Part 3, Chemical Methods." Soil Science Society of America, Madison, WI, 1996, pp. 417-435.

(56) References Cited

OTHER PUBLICATIONS

Rodriguez-Freire, L. et al. "Post Gold King Mine spill investigation of metal stability in water and sediments of the Animas River watershed." Environmental Science and Technology 2016, 50, 11539-11548.

Royal Society of Chemistry, "Portable X-ray fluorescence analysis." Analytical Methods Committee Technical Brief No. 41. 2009, Available online at http://www.rsc.org/images/portable-x-ray-fluorescence-analysis-technical-brief-41_tcm-18-214830.pdf.

Sacristán, D. et al. "Proximal sensing of Cu in soil and lettuce using portable X-ray fluorescence spectrometry." Geoderma 2016, 265, 6-11.

Salinity Laboratory Staff, 1954. Diagnosis and Improvement of Saline and Alkali Soils. Agricultural Handbook No. 60. US Department of Agriculture, Washington, DC.

Savitzky, A., et al. "Smoothing and differentiation of data by simplified least squares procedures" Anal. Chem. 1964, 36, 1627-1639.

Sharma, A. et al. "Characterizing soils via portable X-ray fluorescence spectrometer: 3. Soil reaction (pH)." Geoderma 2014, 232-234, 141-147.

Sharma, A. et al. "Characterizing soils via portable X-ray fluorescence spectrometer: 4. Cation exchange capacity (CEC)." Geoderma 2015, 239-240, 130-134.

Simon, M. et al. "Pollution of soils by the toxic spill of a pyrite mine (Aznalcollar, Spain)." Science of the Total Environment 1999, 242, 105-115.

Soltanpour, P.N. et al. "Inductively coupled plasma emission spectrometry and Inductively couple plasma-mass spectrometry." In: Sparks et al. (Eds.), Methods of Soil Analysis—Part 3, Chemical Methods. Soil Science Society of America, Madison, WI, 1996, pp. 91-139.

Swanhart, S. et al. "Soil salinity measurement via portable X-ray fluorescence spectrometry." Soil Sci. 2014, 179 (9). 417-423.

Trujillo-González, J.M. et al. "Heavy metal accumulation related to population density in road dust samples taken from urban sites under different land uses." Sci Total Environ. 2016, 553, 636-642.

US Environmental Protection Agency (US—EPA). "Field portable X-ray fluorescence spectrometry for the determination of elemental concentrations in soil and sediment." 2007, Available online at: https://www.epa.gov/sites/production/files/2015-12/documents/6200.pdf (verified Sep. 20, 2016).

Vidakovic-Cifrek, Z. et al. "Cytogenetic damage in shallot (Allium cepa) root meristems induced by oil industry "high-density brines"". Arch Environ. Contam. Toxicol. 2002, 43, 284-291.

Weindorf, D.C. et al. "Portable X-ray fluorescence spectrometry analysis of soils." In: Hirmas, D. (Ed.). Methods of soil analysis. Soil Science Society of America, Madison, WI. 2016, p. 1-8. doi:10.2136/methods-soil.2015 0033.

Weindorf, D.C. et al. "Advances in portable X-ray fluorescence (PXRF) for environmental, pedological, and agronomic applications." Advances in Agronomy 2014, 128, 1-45.

Weindorf, D.C. et al. "In-situ assessment of metal contamination via portable X-ray fluorescence spectroscopy: Zlatna, Romania." Environmental Pollution 2013a, 182, 92-100.

International Search Report and Written Opinion, PCT/US2020/053367 [ISA/KR] dated Jan. 27, 2021.

Bairi, V.G. et al. "Portable X-ray fluorescence spectroscopy as a rapid screening technique for analysis of TiO2 and ZnO in sunscreens." Spectrochimica Acta Part B, 116 (2016), 21-27.

Causin, V. et al. "The discrimination potential of diffuse-reflectance ultraviolet-visible-near infrared spectrophotometry for the forensic analysis of paper." Forensic Science International, 216 (2012), 163-167.

Chakraborty, S. et al. "Analysis of petroleum contaminated soils by spectral modeling and pure response profile recovery of n-hexane." Environmental. Pollution. 190 (2014):10-18.

Chakraborty, S. et al. "Development of a hybrid proximal sensing method for rapid identification of petroleum contaminated soils." Science of the Total Environment (2015) 514, 399-408.

Chakraborty, S. et al. "Diffuse reflectance spectroscopy for monitoring lead in landfill agricultural soils of India." Geoderma Regional 5, (2015) 77-85.

Chakraborty, S. et al. Rapid identification of oil-contaminated soils using visible near-infrared diffuse reflectance spectroscopy. Journal of Environmental Quality, 39 (2010), 1378-1387.

DeKosky, R. "Developing chemical instruments for environmental use in the twentieth century: Detecting lead in paint using portable X-ray fluorescence spectrometry." Ambix, 56(2) (2009), 138-162.

Gahlaut, A. et al. "Mass spectroscopy: Investigative tool in forensic toxicology." Drug Invention Today, 6 (2014), 21-25.

Grigg, E.C.M. et al. "Infrared spectra of substituted phenanthrolines in the out-of-plane CH deformation region." Australian Journal of Chemistry, 15, (1962) 864-866. (1962).

Hall, G.E.M.et al. "Evaluation of portable X-ray fluorescence (pXRF) in exploration and mining: Phase 1, control reference materials." Geochemistry: Exploration, Environment, Analysis, 14,(2014) 99-123.

Horta, A. et al. "Potential of integrated field spectroscopy and spatialla analysis for enhanced assessment of soil contamination: A prospective review." Geoderma 241-242 (2015), 180-209.

Horta, A., et al. "Potential of integrated field spectroscopy and spatila analysis for enhanced assessment of soil contamination: A prospective review." Geoderma (2015) 241-242, 180-209.

Hu, W. et al. "Metal analysis of agricultural soils via portable X-ray fluorescence spectrometry." Bulletin of Environmental Contamination and Toxicology, 92, (2014) 420-426.

Luo, J. et al. "Properties of Savitzky-Golay digital differentiators." Digital Signal Processing, 15, (2005) 122-136.

McWhirt, A., et al. "Rapid analysis of elemental concentrations in compost via portable X-ray fluorescence spectrometry." Compost Science & Utilization, (2010) 20(3), 185-193.

Perkampus, H.H. et al. "Die fluoreszenz—und phosphoreszenzspektren der phenanthroline." Naturforsch, 23 (1968), 840-848.

Platt, J. R. "Classification of spectra of cata-condensed hydrocarbons." Journal of Physical Chemistry, (1949) 17(19495), 484.

R Development Core Team, R: A Language and Environment for Statistical Computing. R Foundation for Statistical Computing, Vienna, Austria (2014).

Sanchez-Pomales, G. et al. "Rapid determination of silver in nanobased liquid dietary supplements using a portable X-ray fluorescence analyzer." Journal of Agricultural and Food Chemsitry, 61 (2013), 7250-7257.

Scott, J. et al. "Lead contamination in schoolyard soils." Soil Horizonsticulture, 54 (2013) (2),1-4.

The PubChem Project, Chemical structure of acetaminophen. PubChem Compound Database.

The PubChem Project, Chemical structure of caffeine. PubChem Compound Database.

The PubChem Project, Chemical structure of dextromethorphanm. PubChem Compound Database.

The PubChem Project, Chemical structure of diphenhydramine. PubChem Compound Database.

The PubChem Project, Chemical structure of guaifenesin. PubChem Compound Database.

The PubChem Project, Chemical structure of loperamide. PubChem Compound Database.

The PubChem Project, Chemical structure of loratadine. PubChem Compound Database.

The PubChem Project, Chemical structure of meclizine. PubChem Compound Database.

U.S. Environmental Protection Agency, 2015. Field X-Ray Fluorescence Measurement. USEPA, Athens, GA, 2015.

Wagner, P.J. et al. "Deactivation of triplet phenyl alkyl ketones by conjugatively electron-withdrawing substituents." Journal of the American Chemical Society, (1981) 103 (198124), 7329-7335.

Wang, D. et al. "Synthesized use of VisNIR and PXRF for soil characterization: Total carbon and total nitrogen." Geoderma 243-244 (2015), 157-167.

Weindorf, D. C. et al. "Simultaneous assessment of key properties of arid soil by combined PXRF and Vis-NIR data." European Journal of Soil Science, 67 (2016), 173-183.

(56) References Cited

OTHER PUBLICATIONS

Weindorf, D.C. et al. "Direct soil gypsum quantification via portable X-ray fluorescence spectrometry." Soil Sci. Soc. Am. j. 2013b, 77, 2071-2077.
Weindorf, D.C. et al. "Enhanced pedon horizonation using portable X-ray fluorescence spectroscopy." Soil Sci. Soc. Am. J. 2012, 76 (2), 522-531.
Wright, R.J. et al. "Atomic absorption and name emission spectrometry." In: Sparks et al. (Eds.), Methods or Soil Analysis—Part 3, Chemical Methods. Soil Science Society or America, Madison, WI, 1996, pp. 65-90.
Zhu, Y. et al. "Characterizing soils using a portable x-ray fluorescence spectrometer: 1. Soil texture." Geoderma 2011, 167-168, 167-177.
Zhu, Y. et al. "Characterizing surface soil water with field portable diffuse reflectance spectroscopy." Journal of Hydrology 391 (2010) 133-140.

ENHANCED CHEMICAL CHARACTERIZATION OF SOLID MATRICES USING X-RAY FLUORESCENCE AND OPTICAL COLOR REFLECTANCE

CROSS-REFERENCE TO RELATED APPLICATIONS

This patent application claims priority to and is a: (1) non-provisional patent application of U.S. provisional patent application Ser. No. 62/912,387 filed on Oct. 8, 2019 entitled "Enhanced Chemical Characterization of Solid Matrices using X-Ray Fluorescence and Optical Color Reflectance"; and (2) a continuation-in-part patent application of U.S. patent application Ser. No. 16/715,374 filed on Dec. 16, 2019 entitled "Portable Apparatus for Liquid Chemical Characterization," which is a divisional patent application of U.S. patent application Ser. No. 16/165,472 filed on Oct. 19, 2018 entitled "Portable Apparatus for Liquid Chemical Characterization," now U.S. Pat. No. 10,697,953, which is: (a) a non-provisional patent application of U.S. provisional patent application Ser. No. 62/575,498 filed on Oct. 22, 2017; and (b) a continuation-in-part application of U.S. patent application Ser. No. 15/319,816 filed on Dec. 19, 2016 entitled "Portable Apparatus for Soil Chemical Characterization," now U.S. Pat. No. 10,107,770, which is a U.S. national phase application of PCT patent application PCT/US2015/036537 filed on Jun. 18, 2015, which claims priority to U.S. provisional patent application Ser. No. 62/013,692 filed on Jun. 18, 2014.

This patent application is also related to U.S. patent application Ser. No. 16/715,681 filed on Dec. 16, 2019 entitled "Portable Apparatus for Determining an Elemental Composition of a Sample."

All of the foregoing patent applications are hereby incorporated by reference in their entirety.

INCORPORATION-BY-REFERENCE OF MATERIALS FILED ON COMPACT DISC

None.

TECHNICAL FIELD OF THE INVENTION

The present invention relates generally to the field of chemical analysis and, more particularly, to an apparatus and method for enhanced chemical characterization of solid matrices using X-ray fluorescence and optical color reflectance.

STATEMENT OF FEDERALLY FUNDED RESEARCH

None.

BACKGROUND OF THE INVENTION

Coal is a critical natural resource for power production worldwide. The World Coal Association (2019) estimates that coal reserves approach 1.1 trillion tons worldwide; over 7,269 million tons of hard coal are produced annually, along with 787 million tons of lignite. In the United States in 2017, the Energy Information Agency (2018) reported total United States coal production was 1,058 million short tons (MMst), a decrease of 0.9% from 2016. Coal mining employed 53,051 people in the United States in 2017 (Energy Information Agency, 2018). Furthermore, 92.8% of coal production was used to supply 789 coal-fired power generators operating in the United States (Energy Information Agency, 2018; 2019). Collectively, they account for 279,221 megawatts of power production, roughly 23% of US power production in 2017 (Energy Information Agency, 2019). Notably, there are several different types of coal mined both domestically and internationally. Anthracite is a hard black coal with a C content of ~85%-90% in its natural state. Prime anthracite averages ~0.4% S with volatiles constituting between 4% to 6% by weight. Anthracite seams are typically between 20 to 25 m thick. Historically, this type of coal has been used in the global steel industry and in water filtration (USGS, 2019; Buchsbaum, 2011). Bituminous coal is a black or dark brown coal, often used in steam-electric power generation (USGS, 2019). Additionally, bituminous coal has higher activation energy and ignition temperature than lignite (Guo et al., 2019). Lignite is a low grade, soft coal used primarily as fuel for steam-electric power generation often containing appreciable S deposits within its matrix and a lower C content relative to the two aforementioned coals (USGS, 2019; Indiana Center for Coal Technology Research, 2008). Finally, lignite features the highest moisture content and lowest heat content generation of the major types of coal. Table 1 summarizes the key physicochemical properties of the major types of coal (Indiana Center for Coal Technology Research, 2008).

TABLE 1

Common physicochemical properties of coal
(Indiana Center for Coal Technology Research, 2008)

| | Anthracite | Bituminous | Lignite |
|---|---|---|---|
| Heat Content (kJ) | 13,700-15,800 | 11,600-15,800 | 4,200-8,700 |
| Moisture (%) | <15 | 2-15 | 30-60 |
| Fixed Carbon (%) | 85-98 | 45-85 | 25-35 |
| Ash (%) | 10-20 | 3-12 | 10-50 |
| Sulfur (%) | 0.6-0.8 | 0.7-4.0 | 0.4-1.0 |
| Chlorine (mg kg$^{-1}$) | ~340 | ~340 | ~120 |

Over the last three decades, concerns over pollution (e.g., heavy metals, acid gasses, sulfur dioxide, etc.) caused by coal combustion have grown (US-EPA, 2019). Specifically, the burning of lignite has been linked to acid rain, whereby sulfur dioxide combines with water to form sulfuric acid ($H_2SO_4$), a strong, caustic acid. This greatly exceeds the mild acidity of rain falling through unpolluted air where carbonic acid (a weak acid) is generated (Likens et al., 1972). In areas of the United States where limestone is commonplace or soils are rife with secondary carbonates, appreciable buffering capacity of the acid rain is provided. Yet in areas of the Eastern United States, buffering capacity is limited, and acid rain can quickly lower the pH of soils and associated surface waters (Glass et al., 1982). Concerns over this environmental threat have led to more stringent regulations of coal-fired power plants (Kolstad, 1990).

Traditionally, lignite production has relied upon laboratory analysis for determination of S content in the mined coal (e.g., Methods D3177, D4239; ASTM, 2007; 2019). Sulfur content can vary considerably across deposits owing to a number of factors imbued at the time of deposit formation. Recently, proximal sensing technologies such as portable X-ray fluorescence (PXRF) spectrometry have quickly gained in popularity for soil (Weindorf et al., 2014; Chakraborty et al., 2017), geochemical (Koch et al., 2017), and environmental quality (Paulette et al., 2015) assessment. Contemporary PXRF units commonly utilize a silicon drift detector for analysis of light elements, S among them. For example, Weindorf et al. (2013) used PXRF analysis of S as a proxy for gypsum determination in soils; they reported an $R^2$ of 0.912 relative to traditional laboratory (thermogravimetry) analysis. A few studies have also used PXRF for analysis of coal. Ward et al. (2018a) developed custom user factors for application in an Olympus DP-6000 PXRF which was used to evaluate coal core samples from Australia. They found that coal samples with S content >0.6% offered relatively good agreement with traditional laboratory analysis while in samples with <0.6% S, PXRF tended to inflate reported S content. They further noted that a PXRF scan dwell time of 30 s appears to be adequate for most elemental characterization. In a complimentary study, Ward et al. (2018b) used an iTrax core scanner to characterize coal cores in Australia. They note that mineral efflorescence coatings on the surface of scanned cores may substantively influence the results obtained. Notably, both studies by Ward et al. (2018a, 2018b) were constrained by limited sample numbers. While promising, newer advances in proximal sensors have shown that combinations of PXRF with optical methods such as visible near infrared diffuse reflectance spectrometry (VisNIR DRS) (Aldabaa et al., 2015; Horta et al., 2015; Wang et al., 2015; Weindorf and Chakraborty, 2018) offer substantive improvements to predictive accuracy. Using a SPAD-503 color sensor, Moritsuka et al. (2014) established that it could be used to rapidly estimate total C, total N, and active Fe in soils. The NixPro color sensor may offer additional ancillary optical data (Stiglitz et al., 2017). To date, no such combined optical plus X-ray fluorescence approaches have been applied to the characterization lignite sulfur content, nor have proximal sensor characterization of loose coal powders been attempted.

As a result, there is a need for a portable apparatus and method for chemical characterization of samples, namely the sulfur content of coal.

SUMMARY OF THE INVENTION

In one embodiment, the present invention includes a computerized method for determining a content of the one or more elements of a solid matrix that includes providing a x-ray fluorescence (PXRF) spectrometer, a probe connected to the PXRF spectrometer, a color sensor, one or more processors communicably coupled to the PXRF spectrometer and the color sensor, and one or more input/output interfaces communicably coupled to the one or more processors; scanning the solid matrix using the PXRF spectrometer and the color sensor; receiving a PXRF spectra from the PXRF spectrometer and a numerical color data from the color sensor; extracting a value for each of the one or more elements from the PXRF spectra; determining the content of the one or more elements within the solid matrix using the one or more processors and a predictive model that relates the value of each of the one or more values and the numerical color data to the content of the one or more elements within the solid matrix; and providing the content of the one or more elements within the solid matrix to the one or more input/output interfaces.

In one aspect, the solid matrix comprises coal, soil or a combination thereof. In another aspect, the selected one or more elements comprise sulfur and iron. In another aspect, the method further comprises selecting the one or more elements from a list of elements detectable by the PXRF spectrometer. In another aspect, the method further comprises baseline correcting and smoothing the received PXRF spectra. In another aspect, the predictive model uses a partial least squares regression (PLSR) multivariate algorithm, a support vector regression (SVR) multivariate algorithm, or a random forest (RF) regression algorithm. In another aspect, the method further comprises placing the probe in contact with or proximate to the solid matrix. In another aspect, the method further comprises calibrating the predictive model. In another aspect, the method further comprises configuring the PXRF spectrometer to detect the content of the one or more elements within the solid matrix. In another aspect, the scanning, receiving, extracting, determining and providing steps are performed in situ. In another aspect, the method further comprises determining a geographic location of the solid matrix using a space-based satellite navigation system. In another aspect, the method further comprises determining an elevation of the solid matrix. In another aspect, the scanning, receiving, extracting, determining and providing steps are performed on site proximate to where the solid matrix was taken. In another aspect, the x-ray fluorescence (PXRF) spectrometer, the probe, the color sensor, the one or more processors, and the one or more input/output interfaces are integrated into a portable device. In another aspect, the method further comprises drying and grinding the solid matrix. In another aspect, the method further comprises correcting each value for the one or more elements based on a moisture content within the solid matrix. In another aspect, the method further comprises providing a visible near infrared diffuse reflectance (VisNIR) spectroradiometer communicably coupled to the one or more processors; scanning the solid matrix using the VisNIR spectroradiometer; receiving a spectral absorbance caused by a moisture content within the solid matrix from the VisNIR spectroradiometer; and correcting the PXRF spectra for attenuation or interference caused by the moisture content.

In another embodiment, the present invention provides an apparatus that includes: a probe; a x-ray fluorescence (PXRF) spectrometer connected to the probe; a color sensor; one or more processors communicably coupled to the PXRF spectrometer and the color sensor; one or more input/output interfaces communicably coupled to the one or more processors; and the one or more processors scan the liquid sample using the PXRF spectrometer and the color sensor, receiving a PXRF spectra from the PXRF spectrometer and a numerical color data from the color sensor, extract a value for each of the one or more elements from the PXRF spectra, determine the content of the one or more elements within the solid matrix using a predictive model that relates the value for each of the one or more elements and the numerical color data to the content of the one or more elements within the solid matrix, and provide the content of the one or more elements within the solid matrix to the one or more input/output interfaces.

In one aspect, the solid matrix comprises coal, soil or a combination thereof. In another aspect, the one or more elements comprise sulfur and iron. In another aspect, the one or more elements are selected from a list of elements detectable by the PXRF spectrometer. In another aspect, the one or more processors further baseline correct and smooth the received PXRF spectra. In another aspect, the predictive model uses a partial least squares regression (PLSR) multivariate algorithm, a support vector regression (SVR) multivariate algorithm, or a random forest (RF) regression algorithm. In another aspect, the one or more processors further calibrate the predictive model. In another aspect, the one or more processors configure the PXRF spectrometer to detect the content of the one or more elements within the solid matrix. In another aspect, the one or more processors perform the scanning, receiving, extracting, determining and providing steps in situ. In another aspect, the one or more processors further determine a geographic location of the solid matrix using a space-based satellite navigation system. In another aspect, the one or more processors further determine an elevation of the solid matrix. In another aspect, the one or more input/output interfaces comprise a display, a data storage, a printer or a communications interface. In another aspect, the apparatus is portable. In another aspect, the apparatus is used on site proximate to where the solid matrix was taken. In another aspect, one or more processors further correct the value for each of the one or more elements based on a moisture content within the solid matrix. In another aspect, a visible near infrared diffuse reflectance (VisNIR) spectroradiometer is communicably coupled to the one or more processors; and the one or more processors scan the solid matrix using the VisNIR spectroradiometer, receive a spectral absorbance caused by a moisture content within the solid matrix from the VisNIR spectroradiometer, and correct the PXRF spectra for attenuation or interference caused by the moisture content. In some embodiments, the computer program includes the features described above in reference to the method and apparatus.

The present invention is described in detail below with reference to the accompanying drawings.

BRIEF DESCRIPTION OF THE DRAWINGS

The above and further advantages of the invention may be better understood by referring to the following description in conjunction with the accompanying drawings, in which.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Note that these terms may be used interchangeable without limiting the scope of the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

In one embodiment of the present invention, data from an inexpensive optical color sensor with integrated LED light source (e.g., NixPro color sensor) is combined with elemental data from a portable X-ray fluorescence spectrometer (PXRF) for characterizing the chemical composition of solid matrices (e.g., coal, soil, etc.). Quantitative color code data (e.g., CYMK, RGB, XYZ, etc.) serves as auxiliary input data combined with PXRF elemental data via statistical algorithm to predict the chemical composition of the matrix of interest. The combined sensor approach offers more accurate predictions than either sensor in isolation (e.g., higher RPD, R2, RPIQ; lower RMSE).

This embodiment offers more accurate chemical composition prediction than either sensor in isolation. For example, the NixPro sensor is inexpensive (~$350 USD). Adding the optical reflectance color code data from the NixPro to the PXRF data improves the predictive accuracy of models designed to characterize the chemical composition of solid matrices. This approach is faster and cheaper than traditional wet chemistry methods, and can be conducted in the field, on-site.

Figure 1:
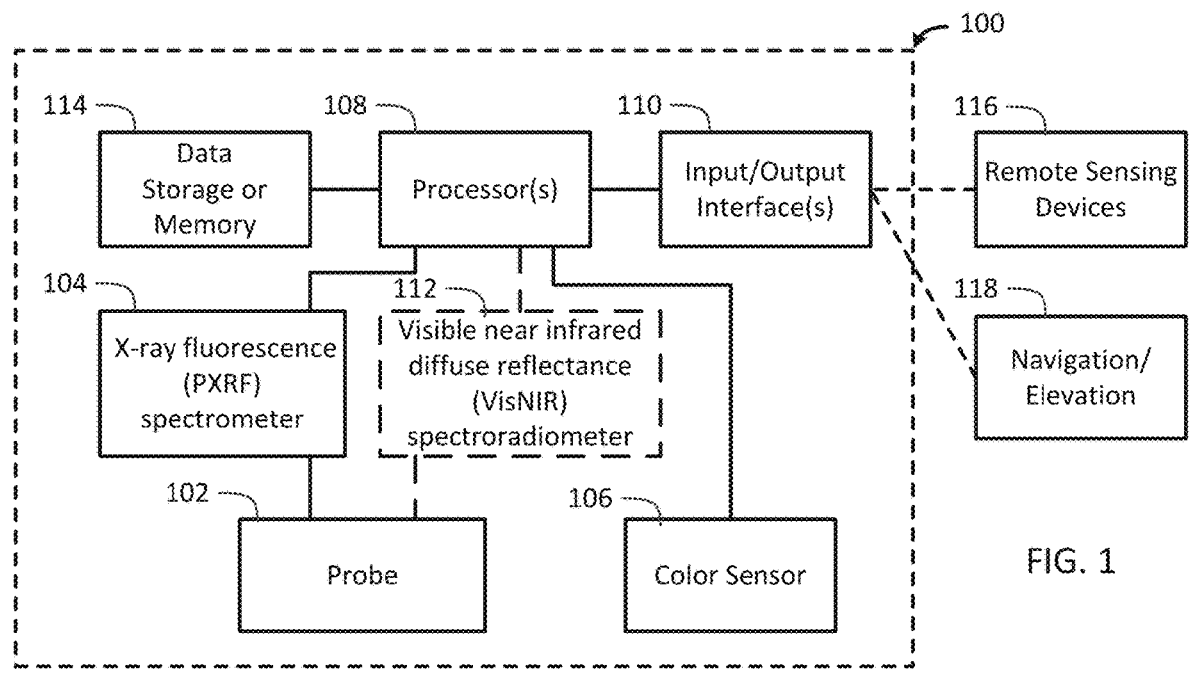
FIG. 1 is a block diagram of an apparatus in accordance with one embodiment of the present invention.

Now referring to FIG. 1, a block diagram of an apparatus 100 in accordance with one embodiment of the present invention is shown. The apparatus 100 includes a probe 102, a x-ray fluorescence (PXRF) spectrometer 104 connected to the probe 102, a color sensor 106, one or more processors 108 communicably coupled to the PXRF spectrometer 104 and the color sensor 106, and one or more input/output interfaces 110 communicably coupled to the one or more processors 108. In some embodiments, the apparatus 100 may include a visible near infrared diffuse reflectance (VisNIR) spectroradiometer 112 connected to the probe 102 and communicably coupled to the one or more processors 108 (see U.S. patent application Ser. No. 15/319,816 filed on Dec. 19, 2016 entitled "Portable Apparatus for Liquid Chemical Characterization"). The one or more processors 108 scan the solid matrix using the PXRF spectrometer 104 and the color sensor 106, receiving a PXRF spectra from the PXRF spectrometer 104 and a numerical color data from the color sensor 106, extract a value for each of the one or more elements from the PXRF spectra, determine the content of the one or more elements within the solid matrix using a predictive model that relates the value for each of the one or more elements and the numerical color data to the content of the one or more elements within the solid matrix, and provide the content of the one or more elements within the solid matrix to the one or more input/output interfaces 110. The apparatus 100 can be portable such that the one or more processors 108 perform the scanning, receiving, extracting, determining and providing steps in situ. Moreover, the scanning, receiving, extracting, determining and providing steps can be performed on site proximate to where the solid matrix was taken.

The one or more processors 108 may transmit or receive data wirelessly via the one or more input/output interfaces 110. The one or more input/output interfaces 110 can be any type of wired or wireless interface to other components, devices or systems either remote or locally located to the apparatus 100. The one or more input/output interfaces 110 may be a display, a data storage, a printer, a communications interface, etc. The one or more processors 108 may also be communicably coupled to a data storage or memory 114. In some embodiments, the one or more processors 108 may automatically select one or more elements from a list of elements detectable by the PXRF spectrometer 104 (as specified by the PXRF spectrometer manufacturer now or in the future), or receive such selection(s) from the one or more input/output interfaces 110 or the data storage or memory 114. The one or more processors 108 may also receive data from a remote sensing device 116, such as a satellite (e.g., Landsat 7, Landsat 8, etc.). For example, the one or more processors 108 may determine a geographic location of the solid matrix using a space-based satellite navigation system 118 or an elevation of the solid matrix.

In one embodiment, the solid matrix is coal, soil or a combination thereof. In another embodiment, the one or more elements can be sulfur and iron. The one or more elements can be selected, automatically or manually, from a list of elements detectable by the PXRF spectrometer. The one or more processors 108 may also baseline correct and smooth the received PXRF spectra, or calibrate the predictive model, configure the PXRF spectrometer to detect the content of the one or more elements within the solid matrix, etc. The predictive model can use a partial least squares regression (PLSR) multivariate algorithm, a support vector regression (SVR) multivariate algorithm, or a random forest (RF) regression algorithm. The one or more processors 108 may correct the value for each of the one or more elements based on a moisture content within the solid matrix. In another embodiment, a VisNIR spectroradiometer 112 is communicably coupled to the one or more processors, and the one or more processors 108 scan the solid matrix using the VisNIR spectroradiometer 112, receive a spectral absorbance caused by a moisture content within the solid matrix from the VisNIR spectroradiometer 112, and correct the PXRF spectra for attenuation or interference caused by the moisture content.

Figure 2:
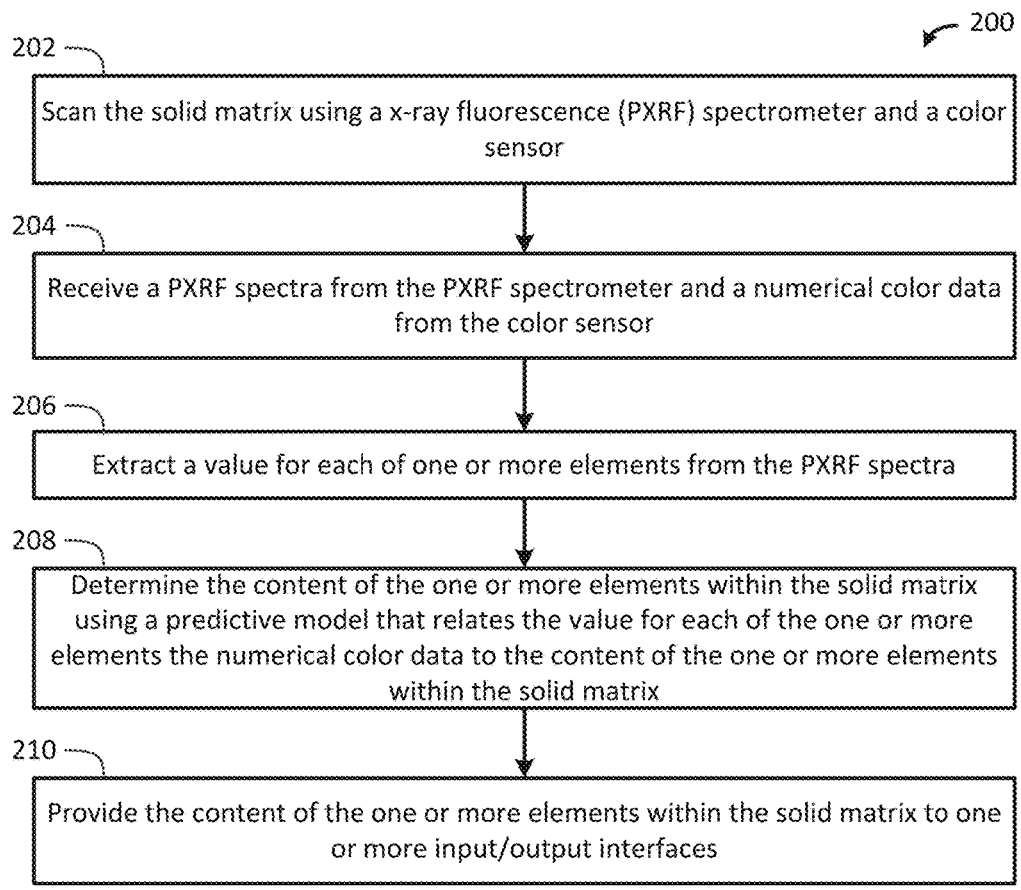
FIG. 2 is a flow chart of a method in accordance with one embodiment of the present invention.

Referring now to FIG. 2, a flow chart of a computerized method 200 for determining a content of the one or more elements of a solid matrix in accordance with one embodiment of the present invention is shown. The method is performed using an apparatus as shown in FIG. 1 or other suitable systems, devices or components. The solid matrix is scanned using a x-ray fluorescence (PXRF) spectrometer and a color sensor in block 202. A PXRF spectra is received from the PXRF spectrometer and a numerical color data is received from the color sensor in block 204. A value for each of the one or more elements are extracted from the PXRF spectra in block 206. The content of the one or more elements within the solid matrix is determined using the one or more processors and a predictive model that relates the value for each of the one or more elements and the numerical color data to the content of the one or more elements within the solid matrix in block 208. The content of the one or more elements within the solid matrix is provided to one or more input/output interfaces in block 210. The scanning, receiving, extracting, determining and providing steps can be performed in situ. Moreover, the scanning, receiving, extracting, determining and providing steps can be performed on site proximate to where the liquid sample was taken. The foregoing method can be performed by a computer program embodied on a non-transitory computer readable medium.

In one embodiment, the solid matrix is coal, soil or a combination thereof. In another embodiment, the one or more elements can be sulfur and iron. The one or more elements can be selected, automatically or manually, from a list of elements detectable by the PXRF spectrometer (as specified by the PXRF spectrometer manufacturer now or in the future). The predictive model can use a partial least squares regression (PLSR) multivariate algorithm, a support vector regression (SVR) multivariate algorithm, or a random forest (RF) regression algorithm.

Additional steps may include: (1) drying and grinding the solid matrix; (2) baseline correcting and smoothing the received PXRF spectra; (3) placing the probe in contact with or proximate to the solid matrix; (4) calibrating the predictive model; (5) configuring the PXRF spectrometer to detect the content of the one or more elements within the solid matrix; (6) determining a geographic location of the solid matrix using a space-based satellite navigation system; (7) determining an elevation of the solid matrix; and/or (8) any other desired step. In addition, the value for each of the one or more elements can be corrected based on a moisture content within the solid matrix. In one embodiment, the method includes providing a VisNIR spectroradiometer communicably coupled to the one or more processors; scanning the solid matrix using the VisNIR spectroradiometer; receiving a spectral absorbance caused by a moisture content within the solid matrix from the VisNIR spectroradiometer; and correcting the PXRF spectra for attenuation or interference caused by the moisture content.

As detailed below, proximal or remotely sensed data can be efficiently used as a proxy for sulfur content assessment in coal, which could result in substantial cost savings relative to traditional lab sulfur content measurements. However, determining sulfur content in coal is only one non-limiting example of how the present invention can be used.

A study was conduced in which four active mines were sampled in North Dakota, USA. A total of 249 samples were dried, powdered, then subjected to laboratory-based dry combustion analysis and scanned with the NixPro, VisNIR, and pXRF sensors. 75% of samples (n=186) were used for model calibration, while 25% (n=63) were used for validation. A strong relationship was observed between dry combustion and PXRF S content (r=0.90). pXRF S and Fe as well as various NixPro color data were the most important variables for predicting S content. When using pXRF data in isolation, random forest regression produced a validation $R^2$ of 0.80 in predicting total S content. Combining PXRF+NixPro improved $R^2$ to 0.85. Dry combustion S+PXRF S and Fe correctly identified the source mine of the lignite at 55.42% via discriminant analysis. Adding the NixPro color data to the PXRF and dry combustion data, the location classification accuracy increased to 63.45%. Even with VisNIR reflectance values of 10-20%, spectral absorbance associated with water at 1,940 nm was still observed. Principal components analysis was unable to resolve the mine source of the coal in PCA space, but several NixPro vectors were closely clustered. In sum, the combination of an inexpensive optical sensor (NixPro, ~$350 USD) with PXRF data successfully augmented the predictive capability of S determination in lignite ex-situ.

Figure 3:
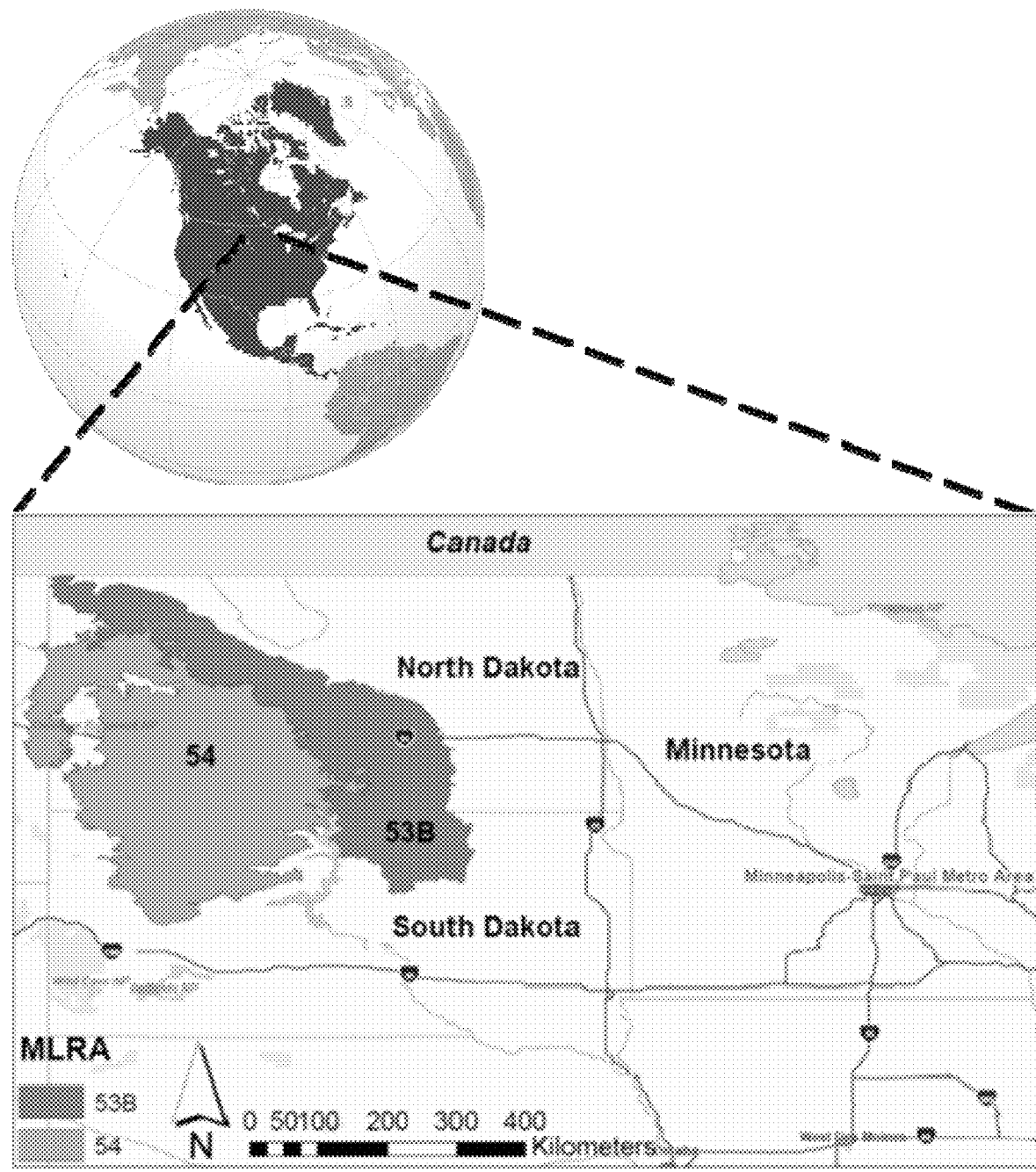
FIG. 3 is a map showing the location of coal sampling sites in Major Land Resource Areas (MLRAs) 53B and 54 in North Dakota, USA.

With deference to protecting producer anonymity, the exact mine sites of sample collection will not be disclosed. However, lignite from multiple active mining sites was collected by hand at four different mines (A, B, C, D) in North Dakota, USA (FIG. 3). Three of the mines (A, B, C) were located in major land resource area (MLRA) 54—Rolling Soft Shale Plain, while the fourth mine (D) was located in MLRA 53B—Central Dark Brown Glaciated Plains (Soil Survey Staff, 2006). Geology of the latter is characterized by glacial till plains and glaciolacustrine deposits with sporadic kettle holes, kames, moraines, and small glacial lakes (Soil Survey Staff, 2006). The former features soft, calcareous shales, siltstones, and sandstones of the Tertiary Fort Union Formation and the Fox Hills and Hell Creek units (Soil Survey Staff, 2006). Soils commonly overlying the lignite deposits are Mollisols and to a lesser extent, Entisols. Most of the area features an ustic soil moisture regime, frigid soil temperature regime, and smectitic to mixed mineralogy. The Koppen climate classification is warm-summer humid continental (Dfb) (Kottek et al., 2006). Surface land use is dominantly corn, canola, and small grain production along with mixed mid-grass pasture used for livestock grazing.

Lignite mining of the area began in the early 1870s; more than 15 billion tons of mineable lignite originally occurred in the area (Oihus, 1983). Today, open pit dragline mining is commonplace is many part of North Dakota. The scale of mines varies substantially, with the largest mines producing >14 million tons of coal annually. Overburden in the area averages 30-50 m in thickness with lignite deposits commonly found in seams one to ten meters thick. Most coal seams in the mines sampled for this study featured deposits of approximately five to seven meters. Coal is ripped or blasted loose after overburden is removed, loaded onto haulers, and used for power production. Following lignite extraction, remediation is undertaken to revegetate the landscape and return it to agricultural or pastoral production.

Field sampling occurred in July 2019 in coordination with personnel from each active mine. Samples were obtained from the active production pit at each site. Collection of lignite samples was random, inclusive of freshly scraped high walls, production piles, and freshly blasted areas. Samples were collected with standard field trowels, shovels, and by hand. Samples collected at each mine were as follows: A (n=59), B (n=60), C (n=65), and D (n=65). Approximately 500 g of each sample was placed into labeled plastic bags for transport to the laboratory for processing.

Figure 4A:
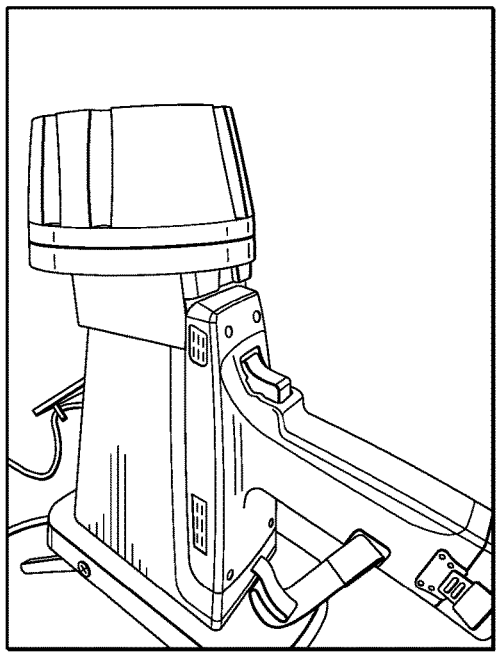
FIGS. 4A-C are images of proximal sensors used for characterization of coal samples at Texas Tech University in accordance with one embodiment of the present invention.
Figure 4B:
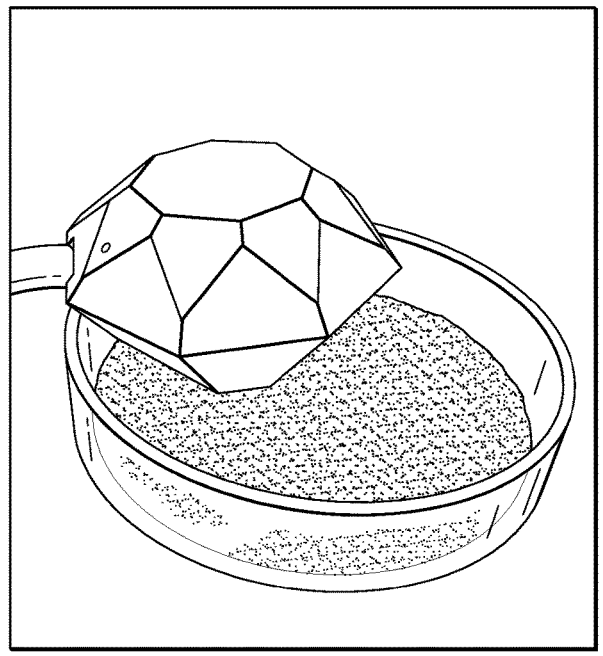

Characterization of the lignite was conducted at Texas Tech University and the University of Minnesota. Prior to analysis, all samples were dried at 65° C. and disaggregated to pass a 2 mm sieve at Dickinson State University. FIGS. 4A-4B are images of proximal sensors used for characterization of coal samples in accordance with one embodiment of the present invention.

FIG. 4A is an image of an Olympus Vanta M series portable X-ray fluorescence spectrometer (PXRF) fitted with a portable test stand. The PXRF spectrometer was used to scan each loose powder per Weindorf and Chakraborty (2016). The PXRF spectrometer features a Rh X-ray tube operated at 10-40 keV in Geochem Mode. Elemental detection was via integrated silicon drift detector. Prior to scanning, the spectrometer was calibrated using a 316 calibration alloy coin. Scanning (dwell) time was set to 45 sec beam$^{-1}$; beams 1 and 2 scanned sequentially such that one complete sample scan was obtained in 90 sec. Key elements of interest for this study were S and Fe. As shown in the inset, powdered coal samples (<2 mm) were massed on a Prolene® thin film (4 μm thickness) (noted with yellow dashed line), which was placed on the stage of a portable test stand, the aperture of the PXRF immediately beneath the stage. The sample stage was covered with a leaded cup to protect the operator during scanning. Instrument performance was verified via scanning of National Institute of Standards and Technology (NIST) certified reference material. PXRF reported- and NIST-certified elemental values follow: NIST 2782 S 2,036/2,000 mg kg$^{-1}$; NIST 2711a Fe 25,813/28,200 mg kg$^{-1}$.

FIG. 4B is an image of an inexpensive (~$350 USD) NIX Pro color sensor (Hamilton, Ontario, Canada) scanning color hex codes of powdered coal. The inset shows the reported numerical color data recorded on a cell phone app. The instrument features integrated 2× 5000K and 2× 6500K High-CRI LEDs light sources designed specifically for color reproduction and is controlled via Bluetooth cell phone application. Spectral acquisition range is 380-730 nm. Measuring geometry was at 45/0° with observer angles of 2° and 10°; instrument aperture is 14 mm. Scanning of each sample is accomplished in <2.5 sec. Color data recorded by the NIX Pro includes: CIELAB, LCH, HEX, RGB, CMYK, ACES, and XYZ; all are interrelated and can be easily converted to uniquely identify individual colors of the matrix being scanned. CIELAB is a color system defined by the Commission Internationale de l'Eclairage (CIE, 2019); it expresses color as three values [L* for lightness ranging from black (0) to white (100), a*) (denoted by A) ranging from green (−) to red (+), and b*) (denoted by B) from blue (−) to yellow (+)] (Sudhakaran, 2013). LCH is another color system defined by the Commission Internationale de l'Eclairage, yet this system uses cylindrical coordinates instead of rectangular coordinates whereby L* indicates lightness, C* (denoted by C) represents chroma, and H reflects hue angle (expressed in degrees) (denoted by H) (Konika Minolta, 2019). By comparison, CMYK data uses a percentage scale (0-100%) to define the contributions of cyan (C), magenta (M), yellow (Y), and black (K) in each matrix color. RGB codes quantitatively establish the content of red (R), green (G), and blue (B, denoted by B.1) colors on a scale from 0 to 255. Linear extensions of RGB are noted in the present dataset as "Lin.sRGB-x". The Academy Color Encoding System (ACES) is a color system advocated by the still and motion picture industry (Arrighetti, 2017; Academy of Motion Picture Arts and Sciences, 2019). It features six color spaces (AP0 Red, AP0 Green, AP0 Blue, AP1 Red, AP1 Green, AP1 Blue); the AP0 represents the smallest set of primaries that includes the entire CIE 1964 standard-observer spectral locus, while the AP1 is conceived with primaries "bent" to be closer to those of display-referred color spaces. Finally, XYZ represents extrapolations of RGB to avoid negative numbers. Y is indicative of luminance, Z is similar to blue, and X is a mix of cone response curves chosen to be orthogonal to luminance and non-negative (Sudhakaran, 2013). To avoid confusion between Y variables from XYZ and CMYK, the latter will be noted as Y.1. Similarly, for the C variables LCH and CMYK, cyan will be noted as C.1. Conversion between the systems aforementioned is offered at the following website: https://www.nixsensor.com/free-color-converter/.

Figure 4C:
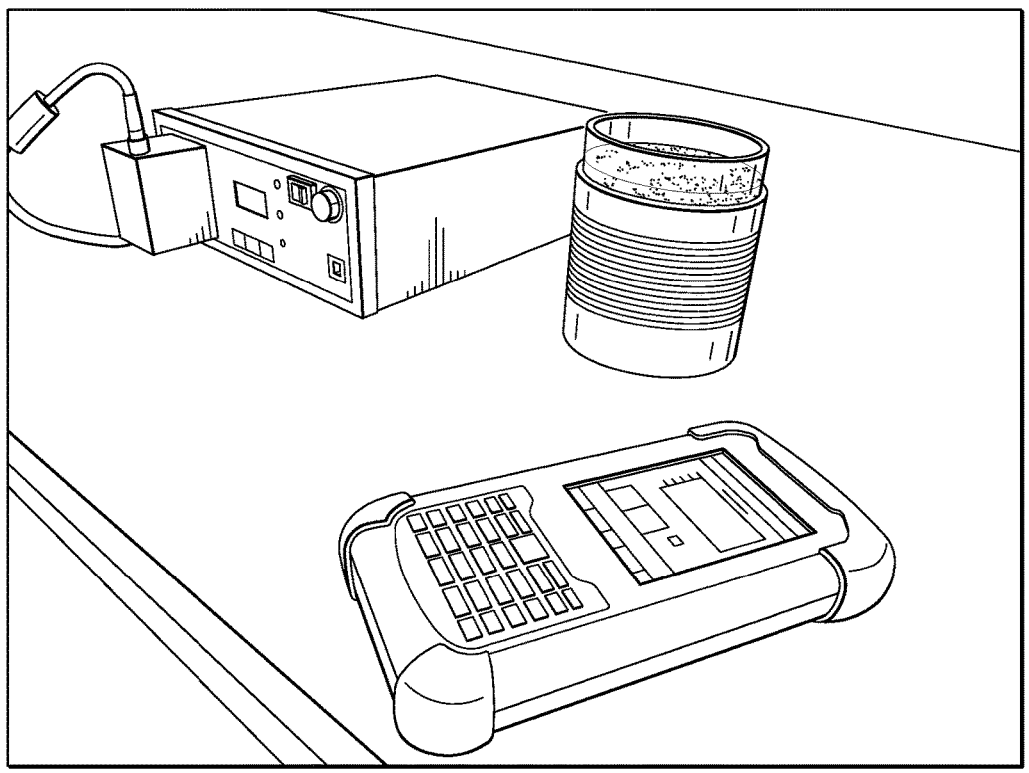

FIG. 4C is an image of a Spectral Evolutions PSR-3500 portable visible near infrared (VisNIR) spectroradiometer (Spectral Evolution, Lawrence, Mass., USA) fitted with a mug lamp and operated by a Getac portable computer. Spectral scanning was from 350 to 2500 nm at 1 nm sampling resolution and spectral resolution of 3.5, 10, and 7 nm from 350 to 1000 nm, 1500 nm, and 2100 nm, respectively. Scanning was facilitated using a mug lamp with 5 W built-in light source. Samples were placed in Duroplan petri dishes for optimal light transmissivity, placed on the mug lamp stage, and scanned from below ensuring no stray light escaped from the sample. Each sample was scanned in triplicate with a 90° rotation between scans; the triplicate scans were then used to create an average spectral curve for each sample. Each individual scan was an average of 10 internal scans every 1.5 sec. An NIST radiance calibration panel was used to white reference the spectroradiometer after scanning every five samples such that fluctuating downwelling irradiance did not cause detector saturation. R version 2.11.0 was used to process raw reflectance spectra using custom R algorithms (Chakraborty et al., 2013, 2014). Wang et al. (2015) summarize these routines as follows: "(i) a parabolic splice to correct for "gaps" between detectors, (ii) averaging replicate spectra, (iii) fitting a weighted (inverse measurement variance) smoothing spline to each spectra with direct extraction of smoothed reflectance at 10 nm intervals."

Finally, powdered samples were subjected to dry combustion analysis on a Rapid CS Cube analyzer (Elementar Americas, Ronkonkoma, N.Y., USA) per Tabatabai (1996). Samples were fine ground to pass a 0.6 mm sieve, precision weighed (70 mg±2 mg) using a four decimal balance, then placed in an autosampler for introduction to the instrument. Tungsten was added at a ratio of 1:1 to facilitate total combustion. Samples were subjected to high temperature (~1,150° C.) combustion, with results reported as total S in mg $kg^{-1}$ or %.

All statistical analyses were executed in R version 3.6.0 (R Core Team, 2019) and XLSTAT version 2019 (Addinsoft, Paris, France). Initially, principal component analysis (PCA) was performed using function 'prcomp' in R to observe the clustering of coal samples coming from four different mines. Generally, PCA indicates the linear combination of the original input variables and essentially analyzes the structure of their correlation matrix. In this study, PCA biplot was produced to investigate the relationship among individual sample and variables used for PCA. Furthermore, in order to evaluate whether a combination of multiple sensors can improve the classification of samples coming from four different mines, discriminant analysis (DA) was executed (Tharwat et al., 2017). In general, DA is a technique that is used by the scientists to analyze the data when the dependent and independent variables are categorical and numeric, respectively. The DA confusion matrix summarizes the reclassification of the observations, and exhibits the percent (%) of correctly classified samples, which indicates the ratio of the number of correctly classified samples over the total number of samples. In this study, DA classification accuracy was compared while using i) only PXRF reported S and Fe, ii) laboratory S+PXRF S and Fe, and iii) combined laboratory S+PXRF S and Fe+NixPro color variables.

Random forest (RF) regression algorithm was used to predict total S (%) using i) PXRF reported S and Fe, ii) NixPro color variables, and iii) combined PXRF reported S and Fe+NixPro color variables to examine whether a combined sensor platform can improve the S prediction accuracy (Breiman, 2001). The 'randomForest' package in R was used to run the RF algorithm and the variable importance plot in RF was produced based on % increase in mean squared error (MSE) to enlist the variables according to their relative influence in model accuracy. The whole dataset was randomly split into calibration (~75%, n=186) and validation (~25%, n=63) sets. The prediction accuracy of the validation set was evaluated based on $R^2$, root mean squared error (RMSE), bias, residual prediction deviation (RPD), and the ratio of performance to interquartile range (RPIQ). In defining RPD as standard deviation (SD) divided by RMSE, Chang et al. (2001) notes that RPDs>2 represent satisfactory models, RPDs between 1.4 and 2.0 reflect fair models, and RPDs<1.4 are non-reliable models. By comparison, RPIQ is defined as the interquartile distance (IQ=Q3–Q1) divided by the standard error of prediction (SEP) (Bellon-Maurel et al., 2010).

Figure 5:
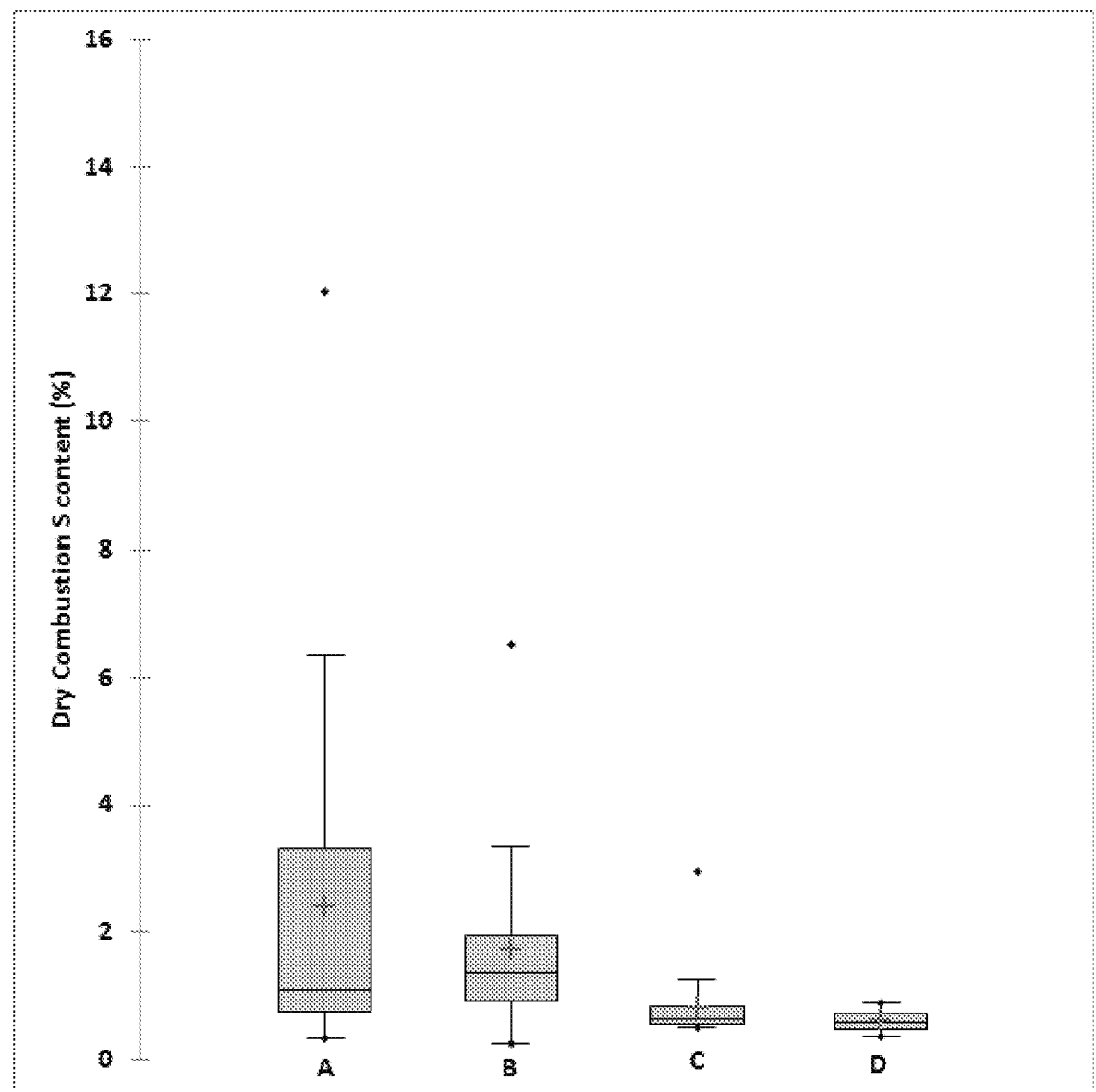
FIG. 5 is a set of box plots illustrating dry combustion S content differences in 249 lignite coal samples from four mines (A, B, C, D) in North Dakota, USA.
Figure 6:
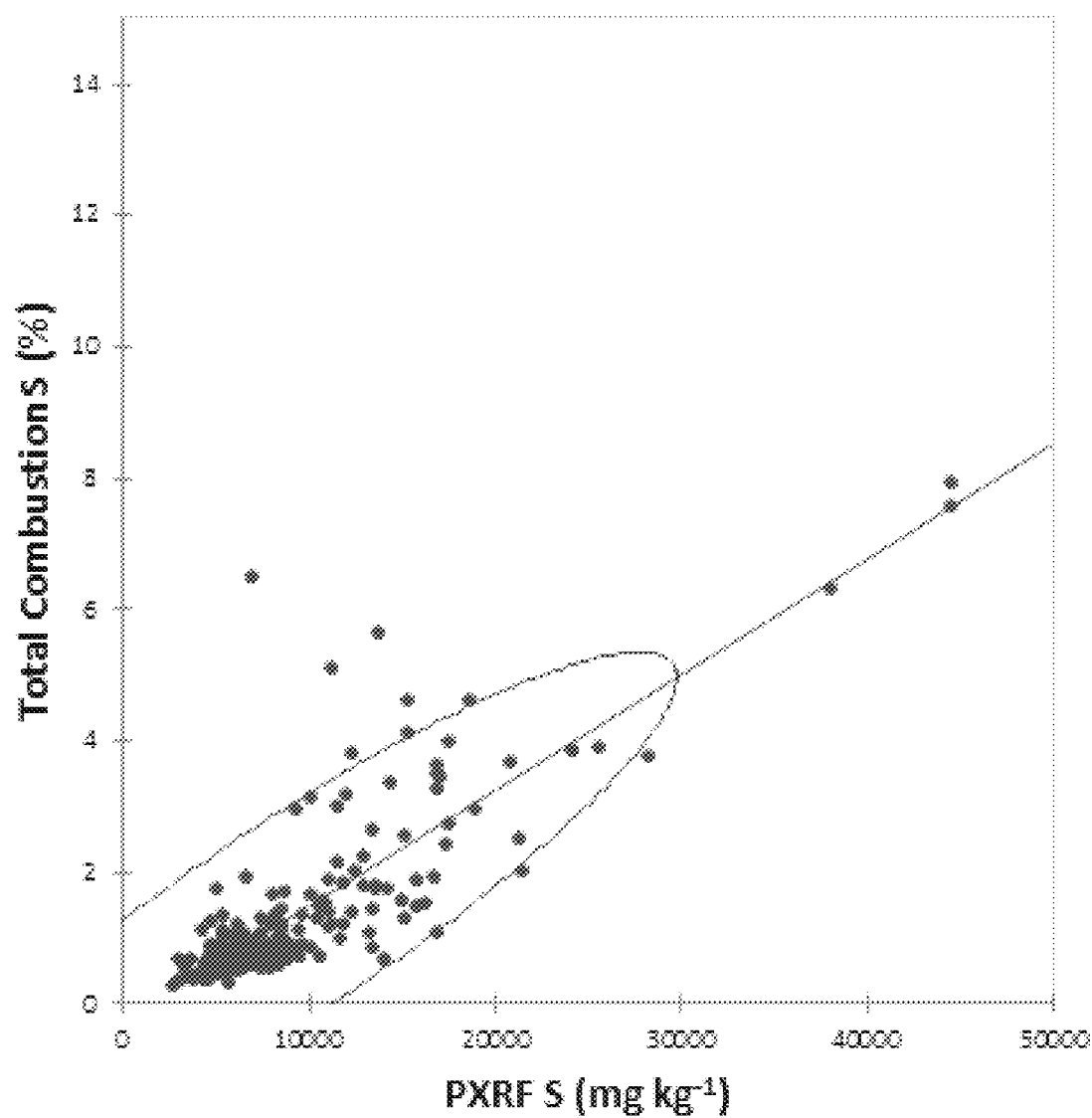
FIG. 6 is a plot showing correlation between total combustion S (%) and PXRF reported S (mg kg$^{-1}$) with confidence ellipse and regression line for 249 lignite coal samples from North Dakota, USA in accordance with one embodiment of the present invention.
Figure 7:
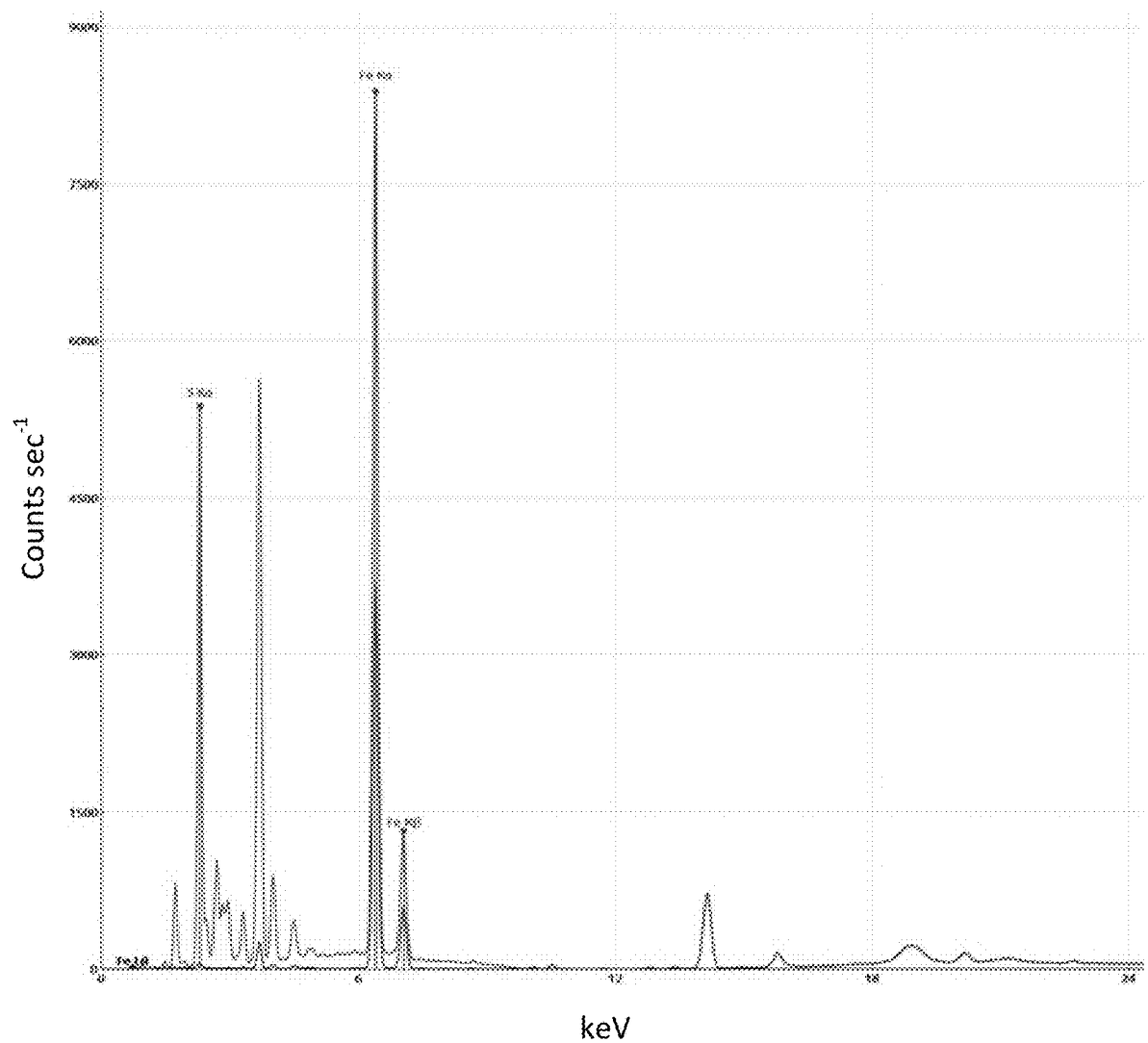
FIG. 7 is a plot showing fluorescence emission energies (keV) for S and Fe determination in lignite coal sample from mine A, North Dakota, USA in accordance with one embodiment of the present invention.

Laboratory combustion analysis revealed a wide variety of S content, ranging from 2,600 mg $kg^{-1}$ to 12.029% with a mean of 1.351%. Furthermore, substantial differences were observed between all four mines for S content (FIG. 5). Similar trends were observed in the PXRF data, with clear differences observed between mines. Summary statistics for PXRF S ranged from 2,707 mg $kg^{-1}$ to 6.8753% with a mean of 9,258 mg $kg^{-1}$. Importantly, the PXRF offered greater resolution than the dry combustion analysis, with limits of detection <50 mk $kg^{-1}$. A strong relationship was observed between dry combustion S and PXRF reported S, namely r=0.90 (FIG. 6). As pyrite ($FeS_2$) was visually observed in many coal samples in-situ, Fe content was also of interest. PXRF reported Fe content ranged from 1,677 mg $kg^{-1}$ to 6.9134% with a mean of 1.2783%. PXRF elemental analyses were obtained at the following fluorescent energies: S $k\alpha1=2.31$ keV; Fe $k\alpha1=6.4$ keV and $k\beta1=7.06$ keV (FIG. 7).

Figure 8A:
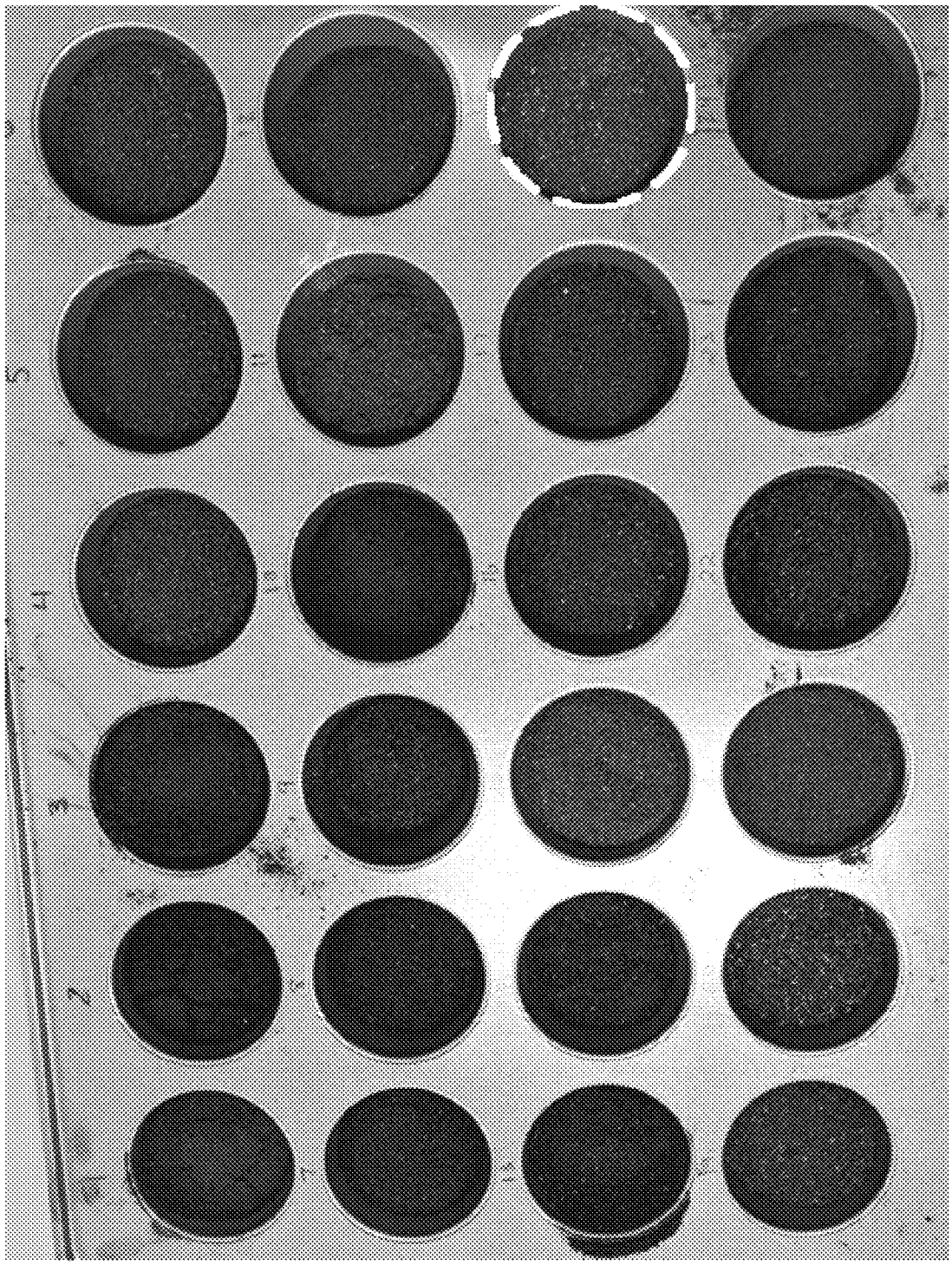
FIG. 8A is an image illustrating the color variation in coal samples after drying (65° C.) and grinding (<2 mm) illustrating the influence of pyrite and overburden mixed into the coal matrix in North Dakota, USA lignite.
Figure 8B:
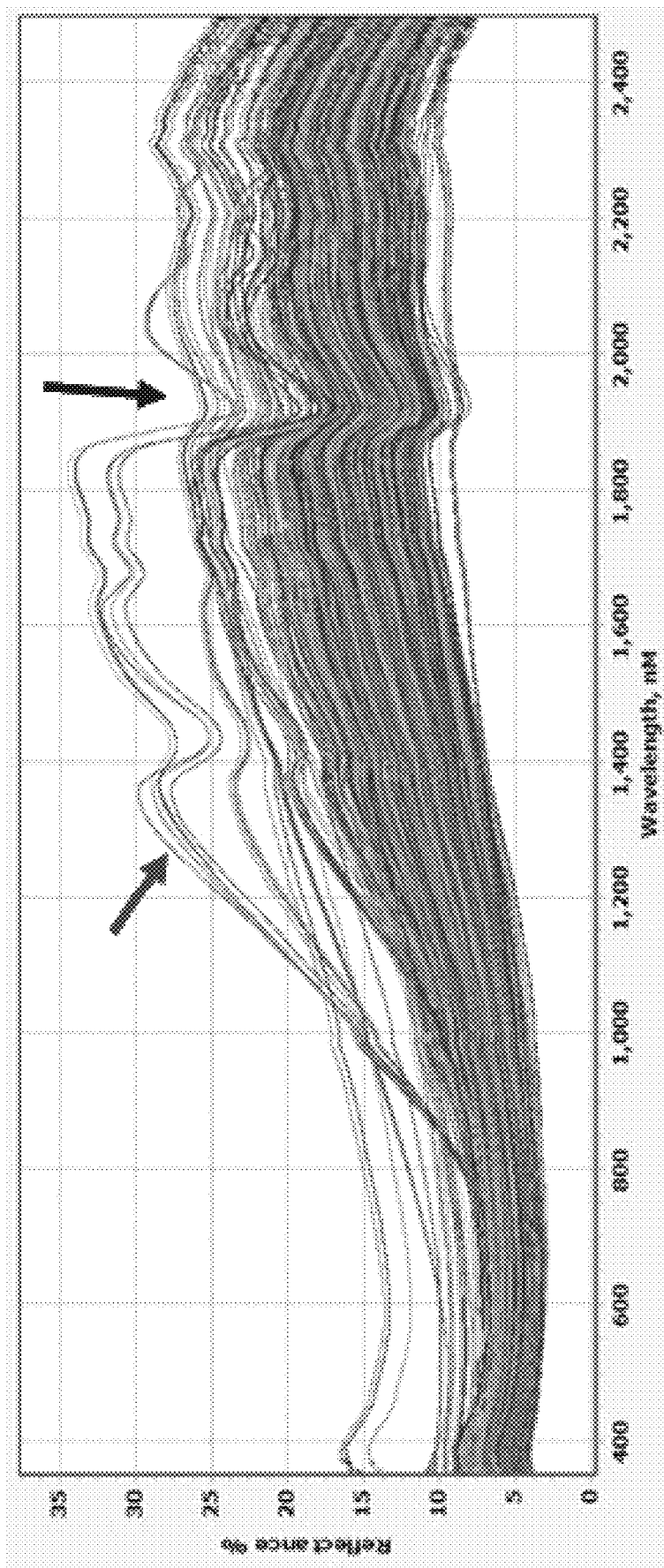
FIG. 8B is a plot showing visible near infrared reflectance spectra of 249 coal samples from the four sampled mines.

The NixPro sensor collected multiple color data codes simultaneously during each scan. Across the 249 coal samples scanned, the NixPro sensor returned color variability as follows: C.1=62-73%; M=60-66%; Y.1=65-72%; K=58-87%. Visual variability of coal matrix color was readily observed following drying and grinding (FIG. 8A). The yellow circle illustrates visual impact of high contents of pyrite (as confirmed by portable X-ray fluorescence elemental data for S and Fe). This is the same sample from mine A illustrated in FIG. 7. Lighter colors were also associated with unique VisNIR reflectance patterns that differed from the majority of dark coal patterns (FIG. 8B). The red arrow illustrates higher reflectance (lighter colored) material suspected of being overburden soil mixed with coal while the blue arrow indicates the moisture absorbance at 1,940 nm (Zhu et al., 2010). The source of lighter color stems from two sources: 1) overburden soil (e.g., clays, silts, sands) interlaced with or washing down onto the darker coal seams below, and 2) the variable presence of pyrite in the coal matrix. The latter was observed extensively at variable degrees as seams or surface luster on black intact coal. The former was observed both intergraded with coal (typically on the upper boundary of the coal seam) as well as surface coating caused by slumping/washing of overburden onto coal from precipitation events.

Despite the low overall VisNIR reflectance (mostly ranging from ~10-20%) and oven drying prior to scanning, VisNIR was able to discern the well-established moisture spectral absorbance at 1,940 nm (Zhu et al., 2010). The absorbance was muted relative to matrix darkening commonly observed in soil (Chakraborty et al., 2019). Nonetheless, it provides an important opportunity for coal moisture characterization in support of in-situ application development of the proximal sensing approach developed herein. Lignite is well-known to contain appreciable moisture. Further, moisture >20% is known to cause attenuation of X-ray fluorescence (US-EPA, 2007; Weindorf et al., 2014). However, combining the two approaches allows for VisNIR to quantify matrix moisture such that a tuning factor could be applied to correct for moisture attenuation of X-ray data in real time.

More specifically, moisture causes X-ray fluorescence attenuation before the fluoresced spectra successfully return to the PXRF aperture for detection/quantification. Coupling the PXRF with VisNIR, we would like to make a claim on using the VisNIR sensor to instantly detect spectral absorbance (e.g., 1940 nm and other wavelengths) caused by moisture in the sample, quantification of that moisture by the VisNIR (already well established in the literature), but then using that moisture determination to correct the PXRF data in real-time for concomitant attenuation of PXRF spectra. In essence, we use the VisNIR moisture determination as a tuning parameter to adjust for interference to the PXRF spectra in real time.

Figure 9:
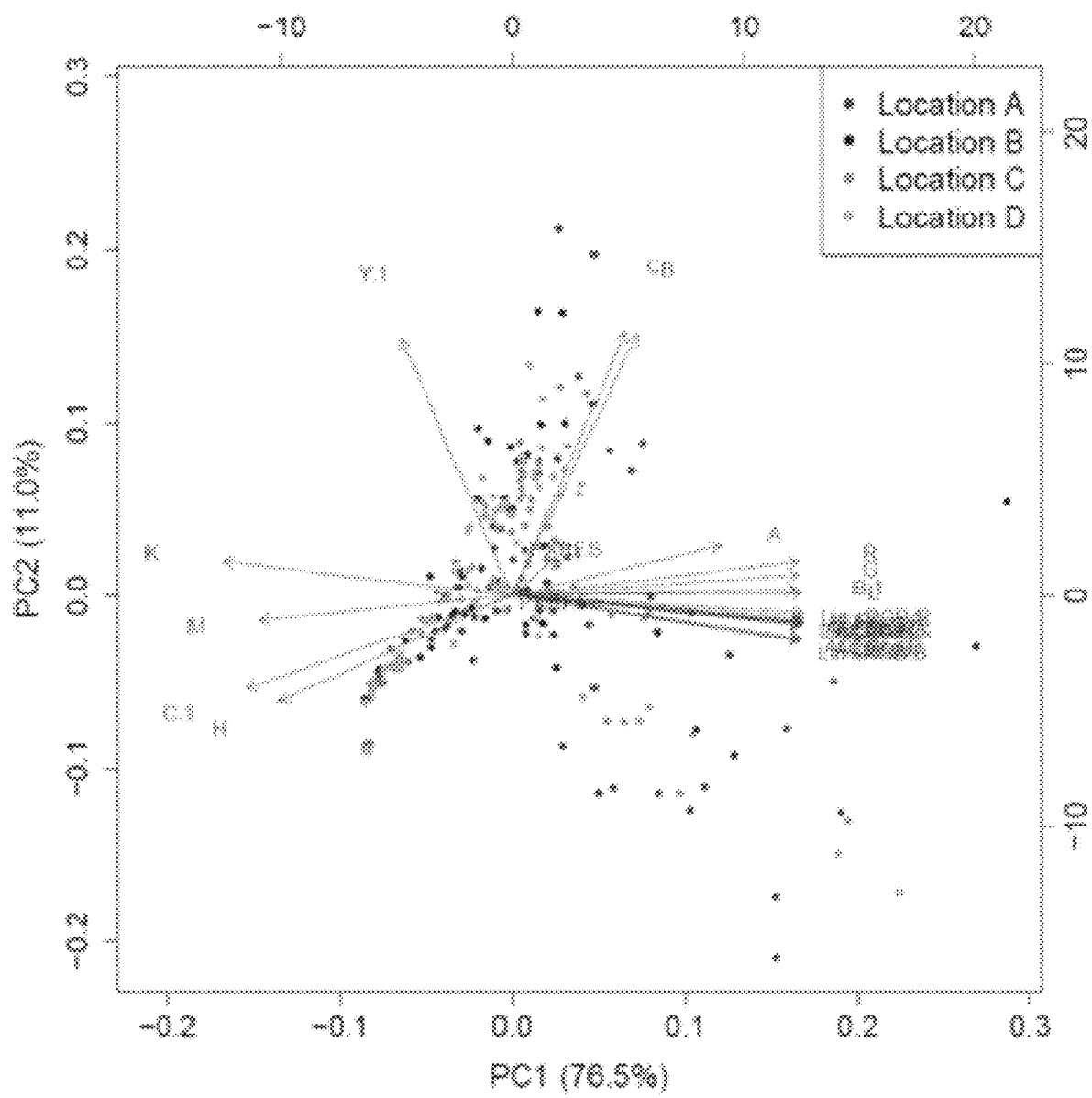
FIG. 9 is a random forest relative variable importance plot while predicting total dry combustion S (%) using portable X-ray fluorescence (PXRF)+NixPro color variables for 249 lignite coal samples from North Dakota, USA in accordance with one embodiment of the present invention.

While examining the PCA biplot (FIG. 9), it was clear that PC1 and PC2 combined explained 88% of the total variance. Apparently, no clear location pattern among the samples was discernible. PC1 mainly showed the direction for all the Lin and ACES variables (as well as R, G, B.1, and L). Samples with large values on PC1 had large values on these variables. PC2 mainly exhibited the Y.1 and C and B directions while samples with large PC2 had large values on these variables. All Lin and ACES variables reported by NixPro were closely correlated to each other. Furthermore, C and B were highly correlated while Y.1 showed comparative less correlation with other NixPro color variables. While C.1, K, M, and H were highly correlated among each other, they showed negative correlation with Lin and ACES variables. The two PXRF variables (S and Fe) showed very small loading values on both PC1 and PC2 and did not exhibit any strong correlation with NixPro color variables.

Results clearly indicated that the use of a combined sensor platform can increase coal sample classification accuracy (Table 2). While using only PXRF reported S and Fe values, DA yielded 52% classification accuracy while the incorporation of laboratory analyzed S content showed a 3% increase in location classification accuracy. Combining laboratory results, PXRF reported S and Fe and NixPro color variables produced the highest classification accuracy (~64%) justifying the predictive power of coal color indices.

TABLE 2

Confusion matrices showing discriminant analysis-based classification accuracy of coal samples collected from four different mines of North Dakota, USA

| from\to | A | B | C | D | Total | % correct |
|---|---|---|---|---|---|---|
| PXRF S and Fe | | | | | | |
| A | 19 | 0 | 38 | 2 | 59 | 32.20% |
| B | 10 | 27 | 21 | 2 | 60 | 45.00% |

TABLE 2-continued

Confusion matrices showing discriminant analysis-based classification accuracy of coal samples collected from four different mines of North Dakota, USA

| from\to | A | B | C | D | Total | % correct |
|---|---|---|---|---|---|---|
| C | 1 | 12 | 37 | 15 | 65 | 56.92% |
| D | 0 | 0 | 18 | 47 | 65 | 72.31% |
| Total | 30 | 39 | 114 | 66 | 249 | 52.21% |
| Laboratory S + PXRF S and Fe | | | | | | |
| A | 25 | 4 | 30 | 0 | 59 | 42.37% |
| B | 12 | 20 | 27 | 1 | 60 | 33.33% |
| C | 1 | 3 | 47 | 14 | 65 | 72.31% |
| D | 0 | 0 | 19 | 46 | 65 | 70.77% |
| Total | 38 | 27 | 123 | 61 | 249 | 55.42% |
| Laboratory S + PXRF S and Fe + NixPro color data | | | | | | |
| A | 34 | 14 | 11 | 0 | 59 | 57.63% |
| B | 13 | 27 | 18 | 2 | 60 | 45.00% |
| C | 2 | 4 | 46 | 13 | 65 | 70.77% |
| D | 3 | 4 | 7 | 51 | 65 | 78.46% |
| Total | 52 | 49 | 82 | 66 | 249 | 63.45% |

While predicting the S content using different sensors, the combined PXRF+NixPro approach produced the best prediction accuracy ($R^2=0.85$) and outperformed the RF models which used PXRF S and Fe ($R^2=0.80$) and NixPro ($R^2=0.18$) in isolation (Table 3). Although using NixPro variables only gave worse results (RPD=1.11) than using PXRF variables (RPD=2.31), combining NixPro and PXRF did improve the RPD statistic (2.56).

TABLE 3

Validation statistics for the random forest models for predicting total S (%) using different proximal sensors in isolation and in combination for coal samples collected from North Dakota, USA

| Model | $R^2$ | RMSE (%) | RPD | Bias (%) | RPIQ |
|---|---|---|---|---|---|
| PXRF | 0.80 | 0.53 | 2.31 | 0.02 | 1.56 |
| NixPro | 0.18 | 1.10 | 1.11 | 0.13 | 0.75 |
| PXRF + NixPro | 0.85 | 0.48 | 2.56 | 0.01 | 1.73 |

Figure 10C:
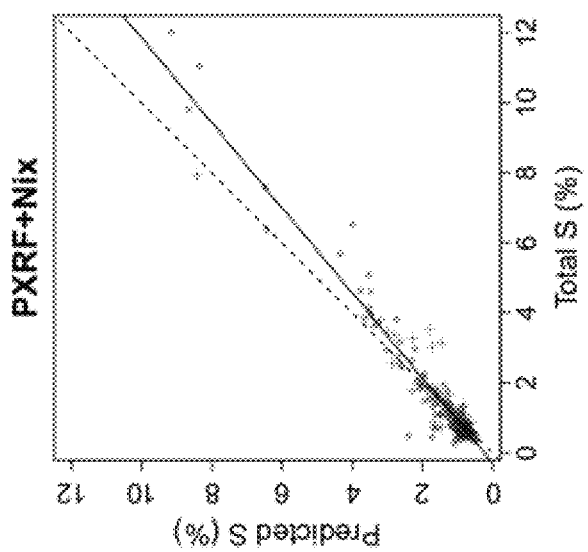
FIGS. 10A-10C are plots showing random forest predicted S (%) vs. total dry combustion S (%) while using PXRF variables (FIG. 10A), NixPro color variables (FIG. 10B), and PXRF+NixPro color variables (FIG. 10C) for 249 lignite coal samples collected from North Dakota, USA in accordance with one embodiment of the present invention.
Figure 10B:
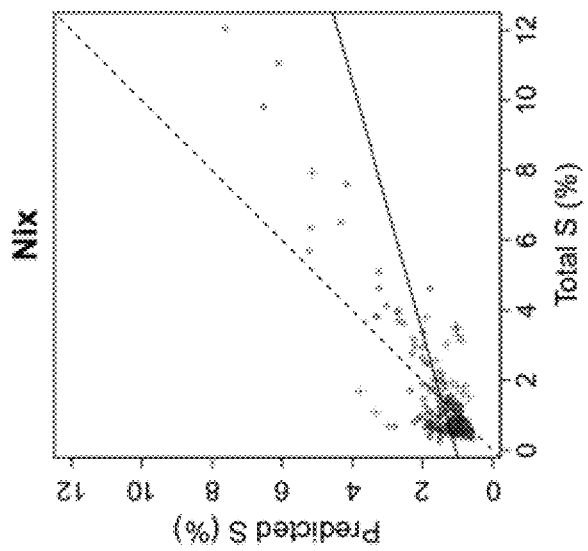
Figure 10A:
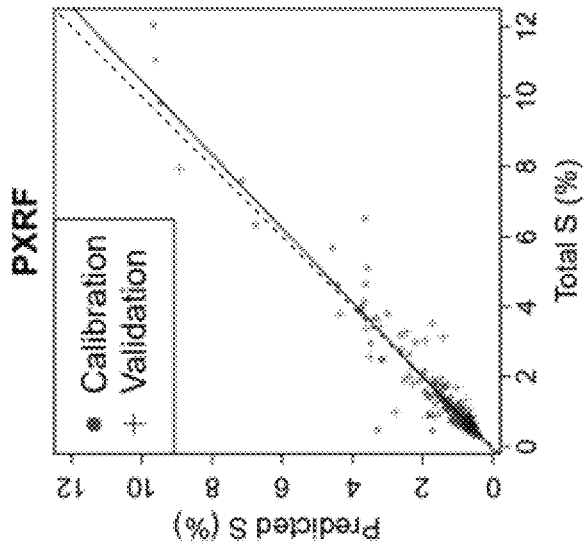
Figure 11:
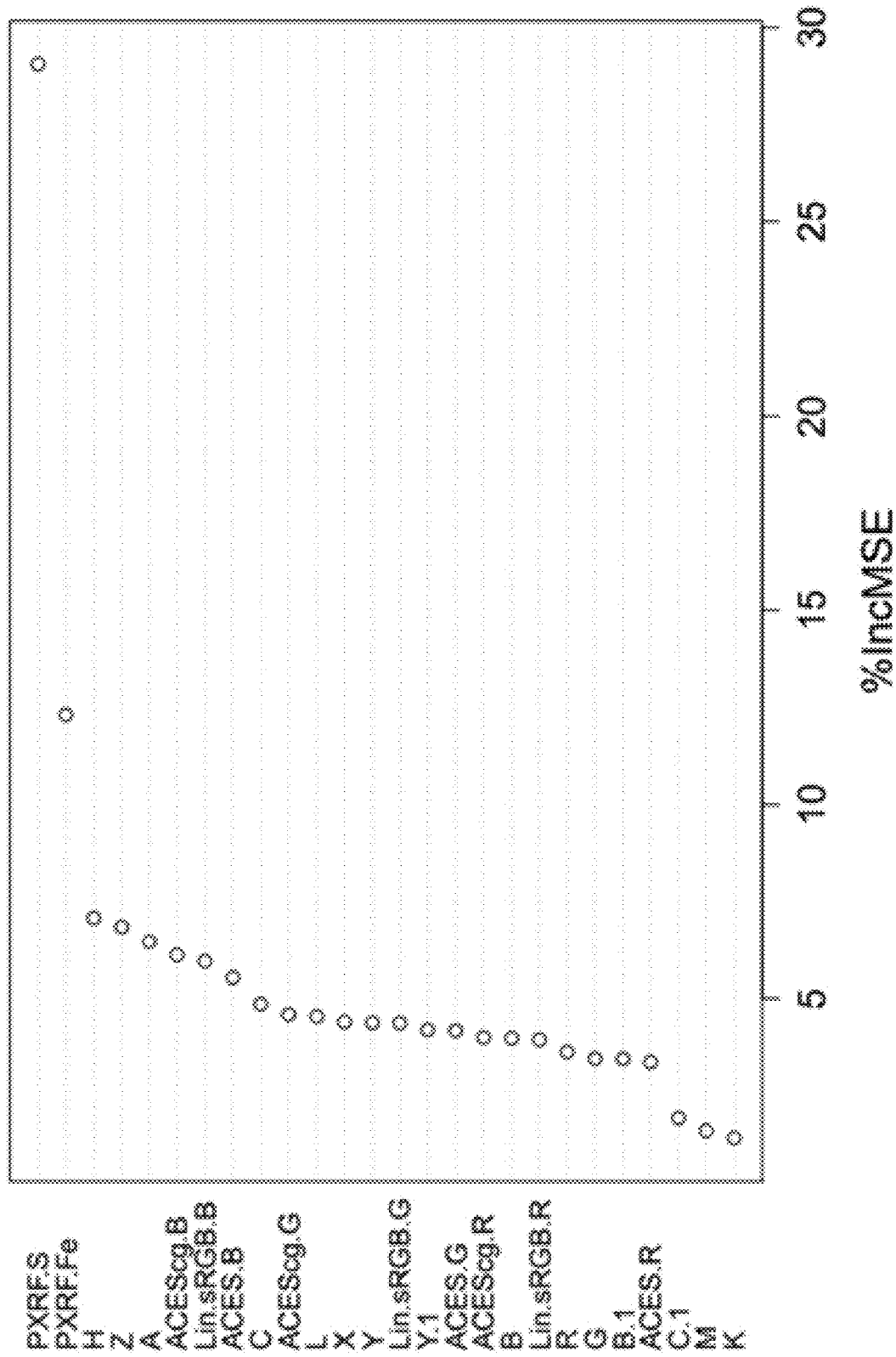
FIG. 11 is a principal components analysis (PCA) biplot of portable X-ray fluorescence (PXRF) and color code variables of 249 lignite coal samples from four mines in North Dakota, USA in accordance with one embodiment of the present invention.

From FIGS. 10A-C, it was evident that by adding NixPro variables into the PXRF model, the prediction on the samples with total S between 1% and 4% appeared slightly better than using only PXRF variables. The dotted line and solid lines represent the 1:1 line and regression line for the validation samples, respectively. Solid red dots and "+" represent calibration and validation samples, respectively. Indeed, the validation samples were more spread around the 1:1 line in PXRF than the PXRF+NixPro model. Note that most of the samples had S content <1% and were predicted reasonably well. The loss in prediction accuracy mainly came from the samples with larger S content while the addition of NixPro color variables improved the prediction accuracy of these samples. This is probably because NixPro explained the variation of S from a different aspect than the underlying mechanism of PXRF model, which contributed to the improvement of prediction accuracy. The RF variable importance plot identified PXRF variables (S and Fe) as the most influential variables followed by H, Z, and A color variables (FIG. 11). While no PCA clustering of mining sites was observed, certain NixPro color sensor vectors were clearly associated in PCA space.

While traditional laboratory analysis is accurate and the current industry standard, the PXRF/optical approach offers high sample throughput and significant time and cost savings. For example, in the present study, two technicians successfully scanned 249 samples using all three proximal sensors in just two days (16 total working hours). The only consumable purchased was the Prolene® thin films used for covering the aperture of the PXRF. A box of 500 films costs $140 USD. Two technicians paid at $10 per hour totaled $320 USD in operator labor. Thus, total cost per sample was ~$1.85 USD. By comparison, dry combustion analysis of the 249 samples cost $3,800 USD; a cost of $15.26 per sample. The cost of drying and grinding of the samples was not considered in the analysis as it is required for both dry combustion and the PXRF/optical approach.

Previous studies (Ward et al., 2018a; 2018b) have employed the use of either wax binders to create pressed pellets for analysis or have scanned intact coal aggregates. However, they specifically advise caution regarding the latter citing the disproportionate influence of effloresced mineral on the coal surface. In fact, such a phenomenon was widely observed at all four of the mines sampled in the present study. Yet results of this study have indicated that grinding and homogenization of coal into a power provides a more uniform matrix for scanning and essentially eliminates the efflorescence bias by equally distributing any mineral pyrite throughout a given sample. Furthermore, strong predictive results using the combined PXRF/optical approach were observed without the need for pelletizing. Ward et al. (2018a) advocated a scanning (dwell) time of 30 sec per beam. While scanning time was 45 sec per beam in the present study, the data collected herein supports the conclusion that scanning time of 30-45 sec produces quality data for coal characterization. The specific gravity of intact lignite (~1.29 g cm$^{-3}$) and soil (~1.33 g cm$^{-3}$) are similar, yet coal powder (as scanned) was substantively less (0.76 g cm$^{-3}$). Thus, differences in matrix density effects may have contributed to data variability as the PXRF was operated in Geochem Mode principally designed for soil and mineral characterization, (Flores, 2013; Weil and Brady, 2017). Custom user factors programmable in the Vanta series PXRF may likely overcome such limitations.

Finally, it was noteworthy that of the four mines sampled, operational personnel at only one mine were familiar with PXRF technology and how it could be used for coal characterization (though even those personnel had never personally used the equipment). The PXRF/optical approach has gained widespread adoption in soil and environmental science within the last decade (Horta et al., 2015).

In conclusion, random forest algorithm integrating PXRF and NixPro data more accurately predicted lignite S content relative to either sensor in isolation. While increases in predictive accuracy afforded by utilizing NixPro color data were modest (5%), the inexpensiveness (~$350) and speed of use (<2.5 sec) of the NixPro sensor make it a worthwhile addition. Beyond enhancing the prediction of S in lignite, adding the NixPro color data to a confusion matrix featuring dry combustion and PXRF data improved classification accuracy by 8%. Despite weak VisNIR reflectance (~10-20%) owing to the dark color of the lignite coal, characteristic absorbance bands at 1,940 nm were observed, even in oven dried materials. This holds important implications for future work whereby the influence of moisture on coal color and fluorescence attenuation may be considered for in-situ studies. Grinding of the samples in this study overcame the efflorescence concerns of Ward et al. (2018b) regarding pyrite seams in the coal. Furthermore, samples were successfully characterized in powdered form, without the need for pellet pressing. Summarily, the combined use of PXRF/ optical methods for characterizing the S content of lignite was successful, saved considerable time and money relative to traditional analysis, and has the potential for in-situ application. Clearly, the ability to rapidly analyze the S content of lignite on-site would be advantageous for coal producers, offering environmental protection with deference to utilizing the lowest possible S content coal for electrical power generation.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

It will be understood by those of skill in the art that information and signals may be represented using any of a variety of different technologies and techniques (e.g., data, instructions, commands, information, signals, bits, symbols, and chips may be represented by voltages, currents, electromagnetic waves, magnetic fields or particles, optical fields or particles, or any combination thereof). Likewise, the various illustrative logical blocks, modules, circuits, and algorithm steps described herein may be implemented as electronic hardware, computer software, or combinations of both, depending on the application and functionality. Moreover, the various logical blocks, modules, and circuits described herein may be implemented or performed with a general purpose processor (e.g., microprocessor, conventional processor, controller, microcontroller, state machine or combination of computing devices), a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein. Similarly, steps of a method or process described herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art.

All of the systems, devices, computer programs, compositions and/or methods disclosed and claimed herein can be made and executed without undue experimentation in light of the present disclosure. While the systems, devices, computer programs, compositions and methods of this invention have been described in terms of preferred embodiments, it will be apparent to those of skill in the art that variations may be applied to the systems, devices, computer programs, compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

Academy of Motion Picture Arts and Sciences, 2019. What is ACES? Available online at: https://www.oscars.org/science-technology/sci-tech-projects/aces (verified 4 Aug. 2019).

Aldabaa, A. A. A., Weindorf, D. C., Chakraborty, S., Sharma, A., Li, B., 2015. Combination of proximal and remote sensing methods for rapid soil salinity quantification. Geoderma 239-240, 34-46.

American Society for Testing and Materials (ASTM), 2007. Method D3177—Standard test methods for total sulfur in the analysis sample of coal and coke. Available online at: https://compass.astm.org/Standards/WITHDRAWN/D3177.htm (verified 31 Jul. 2019).

American Society for Testing and Materials (ASTM), 2019. Method D4239—Standard test method for sulfur in the analysis sample of coal and coke using high temperature tube furnace combustion. Available online at: https://compass.astm.org/download/D4239.905.pdf (verified 31 Jul. 2019).

Arrighetti, W., 2017. The Academy Color Encoding System (ACES): A professional color-management framework for production, post-production, and archival of still and motion pictures. Journal of Imaging DOI: https://doi.org/10.3390/jimaging3040040.

Bellon-Maurel, V., Fernandez-Ahumada, E., Palagos, B., Roger, J. M., McBratney, A., 2010. Critical review of chemometric indicators commonly used for assessing the quality of the prediction of soil attributes by NIR spectroscopy. TrAC Trends in Analytical Chemistry 29(9), 1073-1081.

Breiman, L., 2001. Random forests, Machine Learning 45(1), 5-32.

Buchsbaum, L., 2011. Pennsylvania anthracite re-emerges on the international coal scene. Coal Age. Available online at: https://www.coalage.com/features/pennsylvania-anthracite-re-emerges-on-the-international-coal-scene/ (verified 28 Jul. 2019).

Chakraborty, S., Li, B., Weindorf, D. C., Morgan, C. L. S., 2019. External parameter orthogonalisation of Eastern European VisNIR-DRS soil spectra. Geoderma 337, 65-75.

Chakraborty, S., Weindorf, D. C., Weindorf, C. A., Das, B. S., Li, B., Duda, B., Pennington, S., Ortiz, R., 2017. Semi-quantitative evaluation of secondary carbonates via portable X-ray fluorescence spectrometry. Soil Science Society of America Journal 81, 844-852.

Chakraborty, S., Weindorf, D. C., Li, B., Ali, N., Majumdar, K., Ray, D. P., 2014. Analysis of petroleum contaminated soils by spectral modeling and pure response profile recovery of n-hexane. Environmental Pollution 190, 10-18.

Chakraborty, S., Weindorf, D. C., Ali, N., Li, B., Ge, Y., Darilek, J. L., 2013. Spectral data mining for rapid measurement of organic matter in unsieved moist compost. Appl. Opt. 52, B82-B92.

Chang, C. W., Laird, D. A., Mausbach, M. J., Hurburgh, C. R., 2001. Near-infrared reflectance spectroscopy—Principal components regression analyses of soil properties. Soil Science Society of America Journal 65(2), 480-490.

Energy Information Agency, 2018. Annual coal report. Release date 2 Nov. 2018. Available online at: https://www.eia.gov/coal/annual/ (verified 23 Jul. 2019).

Energy Information Agency, 2019. Existing capacity by energy source, 2017 (Megawatts). Available online at: https://www.eia.gov/electricity/annual/html/epa_04_03.html (verified 23 Jul. 2019).

Flores, R. M., 2013. Coal and coalbed gas: Fueling the future. DOI: https://doi.org/10.1016/B978-0-12-396972-9.00001-X.

Glass, N. R., Arnold, D. E., Galloway, J. N., Hendrey, G. R., Lee, J. J., McFee, W. W., Norton, S. A., Powers, C. F., Rambo, D. L., Schofield, C. L., 1982. Effects of acid precipitation. Environmental Science & Technology 16(3), 162-169.

Guo, L., Zhai, M., Wang, Z., Zhang, Y., Dong, P., 2019. Comparison of bituminous coal and lignite during combustion: Combustion performance, coking, and slagging characteristics. Journal of the Energy Institute 92(3), 802-812.

Horta, A., Malone, B., Stockmann, U., Minasny, B., Bishop, T. F. A., McBratney, A. B., Pallasser, R., Pozza, L., 2015. Potential of integrated field spectroscopy and spatial analysis for enhanced assessment of soil contamination: A prospective review. Geoderma 241-242, 180-209.

Indiana Center for Coal Technology Research, 2008. Coal characteristics. Energy Center at Discovery Park. Purdue University. Available online at; https://www.purdue.edu/discoverypark/energy/assets/pdfs/cctr/outreach/Basics8-CoalCharacteristics-Oct08.pdf (verified 28 Jul. 2019).

International Commission on Illumination (CIE), 2019. Colorimetry—Part 4: CIE 1976 L*A*B colour space. Available online at: http://www.cie.co.at/ (verified 4 Aug. 2019).

Koch, J., Chakraborty, S., Li, B., Moore-Kucera, J., van Deventer, P., Daniell, A., Faul, C., Man, T., Pearson, D., Duda, B., Weindorf, C. A., Weindorf, D. C., 2017. Proximal sensor analysis of mine tailings in South Africa: An exploratory study. Journal of Geochemical Exploration 181, 45-57.

Kolstad, C. D., 1990. Acid deposition regulation and the US coal industry. Energy Policy 18(9), 845-852.

Konika Minolta, 2019. Understanding the CIE L*C*h color space. Available online at: https://sensing.konicaminolta.us/blog/understanding-the-cie-lch-color-space/ (verified 4 Aug. 2019).

Kottek, M., Grieser, J., Beck, C., Rudolf, B., Rubel, F., 2006: World map of the Koppen-Geiger climate classification updated. Meteorol. Z. 15, 259-263.

Likens, G. E., Bormann, F. H., Johnson, N. M., 1972. Acid rain. Environment: Science and Policy for Sustainable Development 14(2), 33-40.

Moritsuka, N., Matsuoka, K., Katsura, K., Sano, S., Yanai, J., 2014. Soil color analysis for statically estimating total carbon, total nitrogen, and active iron contents in Japanese agricultural soils. Soil Science and Plant Nutrition 60, 475-485.

Oihus, C. A., 1983. A history of coal mining in North Dakota, 1873-1982. North Dakota Geological Survey. Available online at: https://www.dmr.nd.gov/ndgs/Publication_List/pdf/EDUCATION%20SERIES/ED-15.pdf (verified 19 Jul. 2019).

Paulette, L., Man, T., Weindorf, D. C., Person, T., 2015. Rapid assessment of soil and contaminant variability via portable X-ray fluorescence spectroscopy: Coma Mica, Romania. Geoderma 243-244, 130-140.

R Core Team, 2019. R: A language and environment for statistical computing. R Foundation for Statistical Computing, Vienna, Austria. Available online at: http://www.Rproject.org (verified 29 May 2019).

Soil Survey Staff, 2006. Major resource regions and major land resource areas of the United States, the Caribbean, and the Pacific Basin. USDA-NRCS. Available online at: https://www.nrcs.usda.gov/wps/portal/nrcs/detail/soils/home/?cid=nrcs142p2_053624 (verified 19 Jul. 2019).

Stiglitz, R., Mikhailova, E., Post, C., Schlautman, M., Sharp, J., 2017. Using an inexpensive color sensor for rapid assessment of soil organic carbon. Geoderma 286, 98-103.

Sudhakaran, S., 2013. What is the difference between CIE LAB, CIE RGB, CIE xyY, and CIE XYZ? Available online at: https://wolfcrow.com/what-is-the-difference-between-cie-lab-cie-rgb-cie-xyy-and-cie-xyz/ (verified 4 Aug. 2019).

Tabatabai, M. A., 1996. Sulfur. In: Sparks, D. L., Page, A. L., Helmke, P. A., Loeppert, R. H., editors, Methods of Soil Analysis Part 3—Chemical Methods, SSSA Book Ser. 5.3. SSSA, ASA, Madison, Wis. p. 921-960. doi:10.2136/sssabookser5.3.c33

Tharwat, A., Gaber, T., Ibrahim, A., Hassanien, A. E., 2017. Linear discriminant analysis: A detailed tutorial. AI Commun. 30(2), 169-190.

United States Environmental Protection Agency (US-EPA), 2019. Cleaner power plants. Available online at: https://www.epa.gov/mats/cleaner-power-plants (verified 23 Jul. 2019).

United States Environmental Protection Agency (US-EPA), 2007. Method 6200—Field portable X-ray fluorescence spectrometry for the determination of elemental concentrations in soil and sediment. Available online at: https://www.epa.gov/sites/production/files/2015-12/documents/6200.pdf (verified 4 Aug. 2019).

United States Geological Survey (USGS), 2019. What are the types of coal? Available online at: https://www.usgs.gov/faqs/what-are-types-coal?qt-news_science_products=0#qt-news_science_products (verified 28 Jul. 2019).

Wang, D., Chakraborty, S., Weindorf, D. C., Li, B., Sharma, A., Paul, S., Ali, M. N., 2015. Synthesized use of VisNIR DRS and PXRF for soil characterization: Total carbon and total N. Geoderma 243-244, 157-167.

Ward, C. R., Kelloway, S. J., Vohra, J., French, D., Cohen, D. R., Marjo, C. E., Wainwright, I. E., 2018a. In-situ inorganic analysis of coal seams using a hand-held field-portable XRF analyser. International Journal of Coal Geology 191, 172-188.

Ward, C. R., Kelloway, S. J., French, D., Wainwright, I. E., Marjo, C., Cohen, D. R., 2018b. Profiling of inorganic elements in coal seams using laboratory-based core scanning X-ray fluorescence techniques. International Journal of Coal Geology 191, 158-171.

Weil, R. R., Brady, N.C., 2017. The nature and properties of soils. 15th ed. Pearson, N.Y.

Weindorf, D. C., Chakraborty, S., 2018. Portable apparatus for soil chemical characterization. U.S. Pat. No. 10,107,770 B2. Date of patent: 23 Oct. 2018.

Weindorf, D. C., Chakraborty, S., 2016. Portable X-ray fluorescence spectrometry analysis of soils. In: Hirmas, D. (Ed.). Methods of soil analysis. Soil Science Society of America, Madison, Wis. p. 1-8. doi:10.2136/methodssoil.2015.0033.

Weindorf, D. C., Bakr, N., Zhu, Y., 2014. Advances in portable X-ray fluorescence (PXRF) for environmental, pedological, and agronomic applications. Advances in Agronomy 128, 1-45.

Weindorf, D. C., Herrero, J., Castañeda, C., Bakr, N., Swanhart, S., 2013. Direct soil gypsum quantification via portable X-ray fluorescence spectrometry. Soil Science Society of America Journal 77(6), 2071-2077.

World Coal Association, 2019. Where is coal found? Available online at: https://www.worldcoal.org/coal/where-coal-found (verified 23 Jul. 2019).

Zhu, Y., Weindorf, D. C., Chakraborty, S., Haggard, B., Johnson, S., Bakr, N., 2010. Characterizing surface soil water with field portable diffuse reflectance spectroscopy. Journal of Hydrology 391, 133-140.

What is claimed is:

1. A computerized method for determining a content of one or more elements within a solid matrix comprising:
   providing a x-ray fluorescence (PXRF) spectrometer, a probe connected to the PXRF spectrometer, a color sensor, one or more processors communicably coupled to the PXRF spectrometer and the color sensor, and one or more input/output interfaces communicably coupled to the one or more processors;
   scanning the solid matrix using the PXRF spectrometer and the color sensor;
   receiving a PXRF spectra from the PXRF spectrometer and a numerical color data from the color sensor;
   extracting a value for each of the one or more elements from the PXRF spectra;
   determining the content of the one or more elements within the solid matrix using the one or more processors and a predictive model that relates the value for each of the one or more elements and the numerical color data to the content of each of the one or more elements within the solid matrix; and providing the content of the one or more elements within the solid matrix to the one or more input/output interfaces.

2. The method as recited in claim 1, wherein the solid matrix comprises coal, soil or a combination thereof.

3. The method as recited in claim 1, wherein the one or more elements comprise sulfur and iron.

4. The method as recited in claim 1, further comprising selecting, automatically or manually, the one or more elements from a list of elements detectable by the PXRF spectrometer.

5. The method as recited in claim 4, wherein:
the solid matrix comprises coal; and
the selected elements comprise sulfur and iron.

6. The method as recited in claim 1, further comprising baseline correcting and smoothing the received PXRF spectra.

7. The method as recited in claim 1, wherein the predictive model uses a partial least squares regression (PLSR) multivariate algorithm, a support vector regression (SVR) multivariate algorithm, or a random forest (RF) regression algorithm.

8. The method as recited in claim 1, further comprising placing the probe in contact with or proximate to the solid matrix.

9. The method as recited in claim 1, further comprising calibrating the predictive model.

10. The method as recited in claim 1, further comprising configuring the PXRF spectrometer to detect the content of the one or more elements within the solid matrix.

11. The method as recited in claim 1, wherein the scanning, receiving, extracting, determining and providing steps are performed in situ.

12. The method as recited in claim 1, further comprising determining a geographic location of the solid matrix using a space-based satellite navigation system.

13. The method as recited in claim 1, further comprising determining an elevation of the solid matrix.

14. The method as recited in claim 1, wherein the scanning, receiving, extracting, determining and providing steps are performed on site proximate to where the solid matrix was taken.

15. The method as recited in claim 1, wherein the x-ray fluorescence (PXRF) spectrometer, the probe, the color sensor, the one or more processors, and the one or more input/output interfaces are integrated into a portable device.

16. The method as recited in claim 1, further comprising drying and grinding the solid matrix.

17. The method as recited in claim 1, further comprising correcting the value for each of the one more elements based on a moisture content within the solid matrix.

18. The method as recited in claim 1, further comprising:
providing a visible near infrared diffuse reflectance (VisNIR) spectroradiometer communicably coupled to the one or more processors;
scanning the solid matrix using the VisNIR spectroradiometer;
receiving a spectral absorbance caused by a moisture content within the solid matrix from the VisNIR spectroradiometer; and
correcting the PXRF spectra for attenuation or interference caused by the moisture content.

19. An apparatus comprising:
a probe;
a x-ray fluorescence (PXRF) spectrometer connected to the probe;
a color sensor;
one or more processors communicably coupled to the PXRF spectrometer and the color sensor;
one or more input/output interfaces communicably coupled to the one or more processors; and
the one or more processors scan the solid matrix using the PXRF spectrometer and the color sensor, receiving a PXRF spectra from the PXRF spectrometer and a numerical color data from the color sensor, extract a value for each one of the elements from the PXRF spectra, determine the content of the one or more elements within the solid matrix using a predictive model that relates the value for each of the one or more elements and the numerical color data to the content of the one or more elements within the solid matrix, and provide the content of the one or more elements within the solid matrix to the one or more input/output interfaces.

20. The apparatus as recited in claim 19, wherein the solid matrix comprises coal, soil or a combination thereof.

21. The apparatus as recited in claim 19, wherein the one or more elements comprise sulfur and iron.

22. The apparatus as recited in claim 19, wherein the one or more elements are selected, automatically or manually, from a list of elements detectable by the PXRF spectrometer.

23. The apparatus as recited in claim 19, wherein the one or more processors further baseline correct and smooth the received PXRF spectra.

24. The apparatus as recited in claim 19, wherein the predictive model uses a partial least squares regression (PLSR) multivariate algorithm, a support vector regression (SVR) multivariate algorithm, or a random forest (RF) regression algorithm.

25. The apparatus as recited in claim 19, wherein the one or more processors further calibrate the predictive model.

26. The apparatus as recited in claim 19, wherein the one or more processors configure the PXRF spectrometer to detect the content of the one or more elements within the solid matrix.

27. The apparatus as recited in claim 19, wherein the one or more processors perform the scanning, receiving, extracting, determining and providing steps in situ.

28. The apparatus as recited in claim 19, wherein the one or more processors further determine a geographic location of the solid matrix using a space-based satellite navigation system.

29. The apparatus as recited in claim 19, wherein the one or more processors further determine an elevation of the solid matrix.

30. The apparatus as recited in claim 19, wherein the one or more input/output interfaces comprise a display, a data storage, a printer or a communications interface.

31. The apparatus as recited in claim 19, wherein the apparatus is portable.

32. The apparatus as recited in claim 19, wherein the apparatus is used on site proximate to where the solid matrix was taken.

33. The apparatus as recited in claim 19, wherein the one or more processors further correct the value for each of the one or more elements based on a moisture content of the solid matrix.

34. The apparatus as recited in claim 19, further comprising:
- a visible near infrared diffuse reflectance (VisNIR) spectroradiometer communicably coupled to the one or more processors; and
- wherein the one or more processors scang the solid matrix using the VisNIR spectroradiometer, receive a spectral absorbance caused by a moisture content of the solid matrix from the VisNIR spectroradiometer, and correct the PXRF spectra for attenuation or interference caused by the moisture contenta VisNIR spectroradiometer communicably coupled to the one or more processors, wherein the moisture content of the solid matrix is determined using the VisNIR spectroradiometer.

* * * * *